US009732148B2

(12) United States Patent
Ayalon et al.

(10) Patent No.: US 9,732,148 B2
(45) Date of Patent: Aug. 15, 2017

(54) ANTI-α-SYNUCLEIN ANTIBODIES AND METHODS OF USE

(71) Applicant: Genentech, Inc., South San Francisco, CA (US)

(72) Inventors: Gai Ayalon, South San Francisco, CA (US); Till Maurer, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/884,542

(22) Filed: Oct. 15, 2015

(65) Prior Publication Data

US 2016/0108113 A1 Apr. 21, 2016

Related U.S. Application Data

(60) Provisional application No. 62/064,867, filed on Oct. 16, 2014.

(51) Int. Cl.
*C07K 16/18* (2006.01)
*A61K 39/395* (2006.01)
*C07H 21/04* (2006.01)

(52) U.S. Cl.
CPC .......... *C07K 16/18* (2013.01); *A61K 39/3955* (2013.01); *C07K 2317/21* (2013.01); *C07K 2317/24* (2013.01); *C07K 2317/34* (2013.01); *C07K 2317/565* (2013.01); *G01N 2800/28* (2013.01); *G01N 2800/2828* (2013.01); *G01N 2800/2835* (2013.01)

(58) Field of Classification Search
CPC ................ C07K 16/18; C07K 2317/21; C07K 2317/24; C07K 2317/34; C07K 2317/56; C07K 2317/565; G01N 2800/28; G01N 2800/2828; G01N 2800/2835; A61K 39/3955; A61K 2039/505
See application file for complete search history.

(56) References Cited

U.S. PATENT DOCUMENTS

| | | | | |
|---|---|---|---|---|
| 8,071,097 | B2 * | 12/2011 | Wu | A01K 67/0278 424/133.1 |
| 8,303,954 | B2 * | 11/2012 | Kubota | C07K 16/18 424/133.1 |
| 8,378,081 | B2 * | 2/2013 | Matsubara | C07K 16/18 424/141.1 |
| 8,586,040 | B2 * | 11/2013 | Wu | A01K 67/0278 424/133.1 |
| 8,613,924 | B2 * | 12/2013 | Yokoseki | C07K 16/18 424/133.1 |
| 8,618,274 | B2 * | 12/2013 | Wu | A01K 67/0278 424/139.1 |
| 8,858,949 | B2 * | 10/2014 | Yokoseki | C07K 16/18 424/172.1 |
| 2005/0196818 | A1 * | 9/2005 | Chilcote | C07K 16/18 435/7.93 |

FOREIGN PATENT DOCUMENTS

| | | | | |
|---|---|---|---|---|
| JP | WO 2011016238 | A1 * | 2/2011 | ............ C07K 16/18 |
| WO | 2004/041067 | A2 | 5/2004 | |
| WO | 2005/013889 | A2 | 2/2005 | |
| WO | 2005/047860 | A2 | 5/2005 | |
| WO | 2006/020581 | A2 | 2/2006 | |
| WO | 2006/045037 | A2 | 4/2006 | |
| WO | 2007/011907 | A2 | 1/2007 | |
| WO | 2007/012061 | A2 | 1/2007 | |
| WO | 2008/103472 | A | 8/2008 | |
| WO | 2009/133521 | A2 | 11/2009 | |
| WO | 2010/069603 | A1 | 6/2010 | |
| WO | 2011/104696 | A1 | 9/2011 | |
| WO | 2011/107544 | A1 | 9/2011 | |
| WO | 2012/051498 | A2 | 4/2012 | |
| WO | 2012/177972 | A1 | 12/2012 | |
| WO | 2013/063516 | A1 | 5/2013 | |
| WO | 2013/066818 | A1 | 5/2013 | |
| WO | 2013/112945 | A1 | 8/2013 | |
| WO | 2014/058924 | A2 | 4/2014 | |

OTHER PUBLICATIONS

Alvarez-Castelao B et al. Epitope mapping of antibodies to alpha-synuclein in LRRK2 mutation carriers, idiopathic Parkinson disease patients, and healthy controls. Frontiers Aging Neuroscience, 6:169, pp. 1-9 (Jul. 2014).*
Giasson BI et al. A panel of epitope-specific antibodies detects protein domains distributed throughout human alpha-synuclein in Lewy bodies of Parkinson's disease. J. Neurosci. Res. 59:528-533 (2000).*
Lindstrom V et al. Immunotherapy targeting alpha-synuclein protofibrils reduced pathology in (Thy-1)-h[A30P] alpha-synuclein mice. Neurobiol. Disease, 69:134-143 (2014).*
Masuda M et al. Inhibition of alpha-synuclein fibril assembly by small molecules: Analysis using epitope-specific antibodies. FEBS Lett. 583:787-791 (2009).*
Mayo Clinic, Parkinson's disease: Prevention; www.mayoclinic. org/diseases-conditions/parkinsons-disease/basics/prevention/con-20028488, retrieved Jan. 8, 2017.*
Mougenot AL et al. Production of a monoclonal antibody, against human alpha-synuclein, in a subpopulation of C57BL/6J mice, presenting a deletion of the alpha-synuclein locus. J. Neurosci. Meth. 192:268-276 (2010).*
Neff F et al. Immunotherapy and naturally occurring autoantibodies in neurodegenerative disorders. Autoimmunity Reviews, 7:501-507 (2008).*
Papachroni KK et al. Autoantibodies to alpha-synuclein in inherited Parkinson's disease. J. Neurochem. 101(3):749-756 (2007).*
Paul WE, editor. Fundamental Immunology, Third Edition. Raven Press, New York, 1993, pp. 292-295.*
Rudikoff S et al. Single amino acid substitution altering antigen-binding specificity. PNAS, 79:1979-1983 (1982).*

(Continued)

*Primary Examiner* — Kimberly A. Ballard

(74) *Attorney, Agent, or Firm* — James E. Nesbitt

(57) ABSTRACT

The present invention relates to anti-alpha-synuclein (anti-α-synuclein) antibodies and methods of using the same.

27 Claims, 12 Drawing Sheets

(56) References Cited

OTHER PUBLICATIONS

Baba et al., "Aggregation of alpha-synuclein in Lewy bodies of sporadic Pakinson's disease and dementia with Lewy bodies" Am J Pathol. 152(4):879-84 (Apr. 1998).

Emadi, S. et al., "Inhibiting Aggregation of α-Synuclein with Human Single Chain Antibody Fragments" Biochemistry 43:2871-2878 (2004).

Emadi, S. et al., "Isolation of a Human Single Chain Antibody Fragment Against Oligomeric α-Synuclein that Inhibits Aggregation and Prevents α-Synuclein-induced Toxicity" Journal of Molecular Biology 368:1132-1144 (2007).

Masliah et al., "Effects of alpha-synuclein immunization in a mouse model of Parkinson's disease" Neuron 46:857-68 (Jun. 16, 2005).

* cited by examiner

MDVFMKGLSKAKEGVVAAAEKTKQGVAEAAGKTKEGVLYV
GSKTKEGVVHGVATVAEKTKEQVTNVGGAVVTGVTAVAQK
TVEGAGSIAAATGFVKKDQLGKNEEGAPQEGILEDMPVDP
DNEAYEMPSEEGYQDYEPEA (SEQ ID NO: 1)

*FIG. 1*

1F7 Light Chain Variable Region

DVVMTQTPLTLSVTIGQPASISCKSSQSLLDSDGKTYLNWLLQRPGQSPKR
LIYLVSKLDSGVPDRFTGSGSGTDFTLKISRVEAEDLGVYYCWQVTHFPHT
FGGGTKLEIK (SEQ ID NO:2)

*FIG. 2A*

1F7 Heavy Chain Variable Region

EVQLQQSGAELVIZPGASVKLSCTASGFNIKDYYMDWVKQRTEQGLEWIA
RIDPEDGETKYAPKFQGKATITADTSSNTAYLQLSSLTSEDTAVYYCRVFD
YWGQGTTLTVSS (SEQ ID NO:3)

*FIG. 2B*

13F3 Light Chain Variable Region

DVLMTQTPLSLPVSLGDQASISCRSSQSIVHSNGNTYLEWYLQKPGQSPKL
LIYKVSNRFSGVPDRFSGSGSGTDFTLKISRVEAEDLGVYYCFQGSHVPPTF
GGGTRLEIK (SEQ ID NO:4)

*FIG. 3A*

13F3 Heavy Chain Variable Region

QVQLQQSGAELVKPGASVKMSCKASGYTFTSYWITWVKKRPGQGLEWIG
DISPGSGSTHYNEKFKSKATLTVDTSSSTAYIQLFSLTSEDSAVYYCAIAQT
TFAYWGQGTLVTVSA (SEQ ID NO:5)

*FIG. 3B*

|  | Monoclonal Antibody 1F7 | Monoclonal Antibody 13F3 |
|---|---|---|
| HVR-L1 | KSSQSLLDSDGKTYLN (SEQ ID NO:6) | RSSQSIVHSNGNTYLE (SEQ ID NO:12) |
| HVR-L2 | LVSKLDS (SEQ ID NO:7) | KVSNRFS (SEQ ID NO:13) |
| HVR-L3 | WQVTHFPHT (SEQ ID NO:8) | FQGSHVPPT (SEQ ID NO:14) |
| HVR-H1 | DYYMD (SEQ ID NO:9) | SYWIT (SEQ ID NO:15) |
| HVR-H2 | RIDPEDGETKYAPKFQG (SEQ ID NO:10) | DISPGSGSTHYNEKFKS (SEQ ID NO:16) |
| HVR-H3 | FDY (SEQ ID NO:11) | AQTTFAY (SEQ ID NO:17) |

ANTI-α-SYNUCLEIN ANTIBODIES AND METHODS OF USE

CROSS REFERENCE TO RELATED APPLICATION

This application claims the benefit of priority of provisional U.S. Application No. 62/064,867 filed Oct. 16, 2014, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 15, 2015, is named P32300_US_1_SL.txt and is 10,667 bytes in size.

FIELD OF THE INVENTION

The present invention relates to anti-alpha-synuclein (anti-α-synuclein) antibodies and methods of using the same.

BACKGROUND

Alpha-synuclein is an abundant presynaptic protein. Point mutations in α-synuclein as well as α-synuclein gene duplications and triplications are associated with Parkinson's disease. (See, e.g., Polymeropoulos et al (1997) Science 276:2045-2047; Kruger et al (1998) Nat Genet 18:106-108; Zarranz et al (2004) Ann Neurol 55:164-173; Kiely et al (2013) Acta Neuropathol 125:753-769; Proukakis et al (2013) Neurology 80:1062-1064; Singleton et al (2003) Science 302:841; and Ibanez et al (2004) Lancet 364:1169-1171.) Additionally, α-synuclein is a major component of intracellular protein aggregates called Lewy bodies, which are pathological hallmarks of neurodegenerative disorders such as, for example, Parkinson's Disease, Lewy body disease, and multiple system atrophy. (See, e.g., Spillantini et al (1997) Nature 388:839-840; Wakabayashi et al (1997) Neurosci Lett 239:45-48; Arawaka et al (1998) Neurology 51:887-889; and Gai et al (1998) Lancet 352:547-548.)

Synucleinopathies comprise a class of neurodegenerative disorders; the term is used broadly to designate a spectrum of progressive degenerative disorders of the human nervous system. Misfolding and intracellular aggregation of α-synuclein are thought to be crucial factors in the pathogenesis of synucleinopathies that share, among other properties, the presence of abnormal α-synuclein immunoreactive inclusion bodies in neurons and/or macroglial cells. Synucleinopathies include, Parkinson's disease (PD), Parkinson's disease dementia (PDD), Lewy body disease (LBD), dementia with Lewy bodies (DLB), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1).

Antibodies to α-synuclein and their use in, inter alia, therapeutic approaches to various synucleinopathies have been described previously. (See, e.g., International Patent Application Publication Nos: WO 1995/06407, WO 2004/041067, WO 2005/013889, WO 2005/047860, WO 2006/020581, WO 2006/045037, WO 2007/012061, WO 2008/103472, WO 2013/063516, WO 2013/112945, WO 2014/058924, WO 2010/069603, WO 2012/177972, WO 2013/066818, WO 2011/104696, WO 2009/133521, WO 2012/051498, WO 2011/107544, WO 2007/011907; see, e.g., Baba et al (1998) Am J Pathol 152:879-884; Emadi et al (2004) Biochemistry 43:2871-2878; Emadi et al (2007) J Mol Biol 368:1132-1144; Masliah et al (2005) Neuron 46:857-868.) However, the need remains for additional novel antibodies to α-synuclein for, inter alia, the effective treatment of synucleinopathies.

SUMMARY

The invention relates to anti-α-synuclein antibodies, compositions comprising anti-α-synuclein antibodies, and methods of using the same.

In some embodiments, an isolated anti-α-synuclein antibody of the present invention comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:9;
  (b) HVR-H2 comprises the amino acid sequence of SEQ ID NO:10;
  (c) HVR-H3 comprises the amino acid sequence of SEQ ID NO:11;
  (d) HVR-L1 comprises the amino acid sequence of SEQ ID NO:6;
  (e) HVR-L2 comprises the amino acid sequence of SEQ ID NO:7; and
  (f) HVR-L3 comprises the amino acid sequence of SEQ ID NO:8.

In some embodiments, the invention provides an isolated anti-α-synuclein antibody comprising: at least one, two, three, four, five and/or six hypervariable region (HVR) sequences, wherein:
  (a) HVR-H1 comprises the amino acid sequence of SEQ ID NO:9;
  (b) HVR-H2 comprises the amino acid sequence of SEQ ID NO:10;
  (c) HVR-H3 comprises the amino acid sequence of SEQ ID NO:11;
  (d) HVR-L1 comprises the amino acid sequence of SEQ ID NOs:6;
  (e) HVR-L2 comprises the amino acid sequence of SEQ ID NO:7; and
  (f) HVR-L3 comprises the amino acid sequence of SEQ ID NO:8.

In some embodiments, the invention provides an isolated anti-α-synuclein antibody comprising three light chain hypervariable regions (HVR-L1, HVR-L2, and LVR-L3), wherein:
  (a) HVR-L1 comprises the amino acid sequence of SEQ ID NO:6;
  (b) HVR-L2 comprises the amino acid sequence of SEQ ID NO:7; and
  (c) HVR-L3 comprises the amino acid sequence of SEQ ID NO:8.

In some embodiments, the invention provides an isolated anti-α-synuclein antibody comprising three heavy chain hypervariable regions (HVR-H1, HVR-H2, and HVR-H3), wherein:
  (a) HVR-H1 comprises the amino acid sequence of SEQ ID NO:9;
  (b) HVR-H2 comprises the amino acid sequence of SEQ ID NO:10; and
  (c) HVR-H3 comprises the amino acid sequence of SEQ ID NO:11.

In some embodiments, the invention provides an isolated anti-α-synuclein antibody comprising: at least one, two, and/or three light chain hypervariable region (HVR) sequences, wherein:
(a) HVR-L1 comprises the amino acid sequence of SEQ ID NO:6;
(b) HVR-L2 comprises the amino acid sequence of SEQ ID NO:7; and
(c) HVR-L3 comprises the amino acid sequence of SEQ ID NO:8.

In some embodiments, the invention provides an isolated anti-α-synuclein antibody comprising: at least one, two, and/or three heavy chain hypervariable region (HVR) sequences, wherein:
(a) HVR-H1 comprises the amino acid sequence of SEQ ID NO:9;
(b) HVR-H2 comprises the amino acid sequence of SEQ ID NO:10; and
(c) HVR-H3 comprises the amino acid sequence of SEQ ID NO:11.

In some embodiments, an isolated anti-α-synuclein antibody of the present invention comprises a heavy chain variable region and a light chain variable region, wherein the heavy chain variable region comprises the amino acid sequence of SEQ ID NO:3, and the light chain variable region comprises the amino acid sequence of SEQ ID NO:2.

In some embodiments, an isolated anti-α-synuclein antibody of the present invention comprises a light chain variable region comprising the amino acid sequence of SEQ ID NO:2.

In some embodiments, an isolated anti-α-synuclein antibody of the present invention comprises a heavy chain variable region comprises the amino acid sequence of SEQ ID NO:3.

In some embodiments, an isolated anti-α-synuclein antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:15;
(b) HVR-H2 comprises the amino acid sequence of SEQ ID NO:16;
(c) HVR-H3 comprises the amino acid sequence of SEQ ID NO:17;
(d) HVR-L1 comprises the amino acid sequence of SEQ ID NO:12;
(e) HVR-L2 comprises the amino acid sequence of SEQ ID NO:13; and
(f) HVR-L3 comprises the amino acid sequence of SEQ ID NO:14.

In some embodiments, the invention provides an isolated anti-α-synuclein antibody comprising: at least one, two, three, four, five and/or six hypervariable region (HVR) sequences, wherein:
(a) HVR-H1 comprises the amino acid sequence of SEQ ID NO:15;
(b) HVR-H2 comprises the amino acid sequence of SEQ ID NO:16;
(c) HVR-H3 comprises the amino acid sequence of SEQ ID NO:17;
(d) HVR-L1 comprises the amino acid sequence of SEQ ID NOs:12;
(e) HVR-L2 comprises the amino acid sequence of SEQ ID NO:13; and
(f) HVR-L3 comprises the amino acid sequence of SEQ ID NO:14.

In some embodiments, the invention provides an isolated anti-α-synuclein antibody comprising three light chain hypervariable regions (HVR-L1, HVR-L2, and LVR-L3), wherein:
(a) HVR-L1 comprises the amino acid sequence of SEQ ID NO:12;
(b) HVR-L2 comprises the amino acid sequence of SEQ ID NO:13; and
(c) HVR-L3 comprises the amino acid sequence of SEQ ID NO:14.

In some embodiments, the invention provides an isolated anti-α-synuclein antibody comprising three heavy chain hypervariable regions (HVR-H1, HVR-H2, and HVR-H3), wherein:
(a) HVR-H1 comprises the amino acid sequence of SEQ ID NO:15;
(b) HVR-H2 comprises the amino acid sequence of SEQ ID NO:16; and
(c) HVR-H3 comprises the amino acid sequence of SEQ ID NO:17.

In some embodiments, the invention provides an isolated anti-α-synuclein antibody comprising: at least one, two, and/or three light chain hypervariable region (HVR) sequences, wherein:
(a) HVR-L1 comprises the amino acid sequence of SEQ ID NO:12;
(b) HVR-L2 comprises the amino acid sequence of SEQ ID NO:13; and
(c) HVR-L3 comprises the amino acid sequence of SEQ ID NO:14.

In some embodiments, the invention provides an isolated anti-α-synuclein antibody comprising: at least one, two, and/or three heavy chain hypervariable region (HVR) sequences, wherein:
(a) HVR-H1 comprises the amino acid sequence of SEQ ID NO:15;
(b) HVR-H2 comprises the amino acid sequence of SEQ ID NO:16; and
(c) HVR-H3 comprises the amino acid sequence of SEQ ID NO:17.

In some embodiments, an isolated anti-α-synuclein antibody of the present invention comprises a heavy chain variable region and a light chain variable region, wherein the heavy chain variable region comprises the amino acid sequence of SEQ ID NO:5, and the light chain variable region comprises the amino acid sequence of SEQ ID NO:4.

In some embodiments, an isolated anti-α-synuclein antibody of the present invention comprises a light chain variable region comprising the amino acid sequence of SEQ ID NO:4.

In some embodiments, an isolated anti-α-synuclein antibody of the present invention comprises a heavy chain variable region comprises the amino acid sequence of SEQ ID NO:5.

An anti-α-synuclein antibody of the present invention binds to an epitope of α-synuclein. In some embodiments, an anti-α-synuclein antibody of the present invention binds to amino acid residues 5, 8-9, 15-22, 28, 39-43, and 78 of human α-synuclein (amino acid residues numbered according to the human α-synuclein amino acid sequence of SEQ ID NO:1; throughout the instant specification). In some embodiments, an anti-α-synuclein antibody of the present invention binds to amino acid residues 5, 8-9, 15-22, 28, and 39-43 of human α-synuclein. In some embodiments, an anti-α-synuclein antibody of the present invention binds to an epitope or region comprising amino acid residues 5-78 of human α-synuclein: (MDVFMKGLSKAKEGVVAAAEK- TKQGVAEAAGKTKEGVLYVGSKTKEGVVHGVAT-VAEKTKEQVTNVGGAVVTGVTAVA; SEQ ID NO:18). In some embodiments, an anti-α-synuclein antibody of the present invention binds to an epitope or region comprising amino acid residues 5-43 of human α-synuclein: (MDVF-MKGLSKAKEGVVAAAEKTKQGVAEAAGKTKEGV-LYVGSK; SEQ ID NO:19).

In some embodiments, an anti-α-synuclein antibody of the present invention binds to an epitope or region comprising amino acid residues 37-51 of human α-synuclein (VLY-VGSKTKEGVVHG; SEQ ID NO:20).

In some embodiments, an anti-α-synuclein antibody of the present invention binds to amino acid residues 104-105, 107, 109-111, 113-116, and 118 of human α-synuclein. In some embodiments, an anti-α-synuclein antibody of the present invention binds to an epitope or region comprising amino acid residues 104-118 of human α-synuclein (GKNEEGAPQEGILEDMPV; SEQ ID NO:21)

In some embodiments, an anti-α-synuclein antibody of the present invention competitively inhibits the binding of reference monoclonal antibody 1F7 to human α-synuclein. In some embodiments, an anti-α-synuclein antibody of the present invention competitively inhibits the binding of reference monoclonal antibody 13F3 to human α-synuclein. In some embodiments, an anti-α-synuclein antibody of the present invention binds to the same epitope on human α-synuclein as reference monoclonal antibody 1F7. In some embodiments, an anti-α-synuclein antibody of the present invention binds to the same epitope on human α-synuclein as reference monoclonal antibody 13F3.

In some embodiments, an anti-α-synuclein antibody of the present invention binds human α-synuclein, wherein the α-synuclein is monomeric or in monomeric form. In other embodiments, an anti-α-synuclein antibody of the present invention binds human α-synuclein, wherein the α-synuclein is oligomeric or in oligomeric or aggregated form.

The invention also provides isolated nucleic acids encoding an anti-α-synuclein antibody of the present invention. The invention also provides vectors comprising a nucleic acid encoding an anti-α-synuclein antibody of the present invention. The invention also provides host cells comprising a nucleic acid or a vector of the present invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example, a mammalian cell, such as a Chinese Hamster Ovary (CHO) cell.

The invention further provides a method of producing an anti-α-synuclein antibody of the present invention. For example, the invention provides methods for making an anti-α-synuclein antibody (which, as defined herein, includes full length antibody and fragments thereof), the method comprising expressing in a suitable host cell a recombinant vector of the invention encoding an anti-α-synuclein antibody or fragments thereof so that the antibody or fragments thereof are produced. In some embodiments, the method comprises culturing a host cell comprising nucleic acid encoding an anti-α-synuclein antibody of the present invention (or fragments thereof) so that the nucleic acid is expressed. The method may further comprise recovering the anti-α-synuclein antibody or fragments thereof from the host cell culture or the host cell culture medium.

The invention also provides a pharmaceutical formulation comprising an anti-α-synuclein antibody of the present invention and a pharmaceutically acceptable carrier. The pharmaceutical formulation may further comprise an additional therapeutic agent (e.g., a different anti-α-synuclein antibody).

The invention also provides compositions comprising an anti-α-synuclein antibody of the present invention. The composition may further comprise an additional therapeutic agent (e.g., a different anti-α-synuclein antibody).

The invention also provides a composition comprising an anti-α-synuclein antibody of the present invention for use in preventing a synucleinopathy. In some embodiments, the invention provides a pharmaceutical composition comprising an anti-α-synuclein antibody of the present invention for use in preventing a synucleinopathy. The invention further provides a composition comprising an anti-α-synuclein antibody of the present invention for use in treating a synucleinopathy. In some embodiments, the invention provides a pharmaceutical composition comprising an anti-α-synuclein antibody of the present invention for use in treating a synucleinopathy.

The invention also provides a composition comprising an anti-α-synuclein antibody of the present invention for use in preventing or delaying the onset of Parkinson's Disease. In some embodiments, the invention provides a pharmaceutical composition comprising an anti-α-synuclein antibody of the present invention for use in preventing or delaying the onset of Parkinson's Disease. The invention further provides a composition comprising an anti-α-synuclein antibody of the present invention for use in treating Parkinson's Disease. In some embodiments, the invention provides a pharmaceutical composition comprising an anti-α-synuclein antibody of the present invention for use in treating Parkinson's Disease.

The invention also provides a composition comprising an anti-α-synuclein antibody of the present invention for use in preventing or delaying the onset of Lewy body disease. In some embodiments, the invention provides a pharmaceutical composition comprising an anti-α-synuclein antibody of the present invention for use in preventing or delaying the onset of Lewy body disease. The invention further provides a composition comprising an anti-α-synuclein antibody of the present invention for use in treating Lewy body disease. In some embodiments, the invention provides a pharmaceutical composition comprising an anti-α-synuclein antibody of the present invention for use in treating Lewy body disease.

The invention also provides a composition comprising an anti-α-synuclein antibody of the present invention for use in preventing or delaying the onset of dementia with Lewy bodies. In some embodiments, the invention provides a pharmaceutical composition comprising an anti-α-synuclein antibody of the present invention for use in preventing or delaying the onset of dementia with Lewy bodies. The invention further provides a composition comprising an anti-α-synuclein antibody of the present invention for use in treating dementia with Lewy bodies. In some embodiments, the invention provides a pharmaceutical composition comprising an anti-α-synuclein antibody of the present invention for use in treating dementia with Lewy bodies.

The invention also provides a composition comprising an anti-α-synuclein antibody of the present invention for use in preventing or delaying the onset of multiple system atrophy. In some embodiments, the invention provides a pharmaceutical composition comprising an anti-α-synuclein antibody of the present invention for use in preventing or delaying the onset of multiple system atrophy. The invention further provides a composition comprising an anti-α-synuclein antibody of the present invention for use in treating multiple system atrophy. In some embodiments, the invention provides a pharmaceutical composition comprising an anti-α- synuclein antibody of the present invention for use in treating multiple system atrophy.

The invention also provides a composition comprising an anti-α-synuclein antibody of the present invention for use in preventing or delaying the onset of pure autonomic failure. In some embodiments, the invention provides a pharmaceutical composition comprising an anti-α-synuclein antibody of the present invention for use in preventing or delaying the onset of pure autonomic failure. The invention further provides a composition comprising an anti-α-synuclein antibody of the present invention for use in treating pure autonomic failure. In some embodiments, the invention provides a pharmaceutical composition comprising an anti-α-synuclein antibody of the present invention for use in treating pure autonomic failure.

The invention also provides a composition comprising an anti-α-synuclein antibody of the present invention for use in preventing or delaying the onset of Parkinson's disease dementia, preventing or delaying the onset of juvenile-onset generalized neuroaxonal dystrophy (Hallervorden-Spatz disease), or preventing or delaying the onset of neurodegeneration with brain iron accumulation type-1 (NBIA-1). In some embodiments, the invention provides a pharmaceutical composition comprising an anti-α-synuclein antibody of the present invention for use in preventing or delaying the onset of Parkinson's disease dementia, preventing or delaying the onset of juvenile-onset generalized neuroaxonal dystrophy (Hallervorden-Spatz disease), or preventing or delaying the onset of neurodegeneration with brain iron accumulation type-1 (NBIA-1). The invention further provides a composition comprising an anti-α-synuclein antibody of the present invention for use in treating Parkinson's disease dementia, treating juvenile-onset generalized neuroaxonal dystrophy (Hallervorden-Spatz disease), or treating neurodegeneration with brain iron accumulation type-1 (NBIA-1). In some embodiments, the invention provides a pharmaceutical composition comprising an anti-α-synuclein antibody of the present invention for use in treating Parkinson's disease dementia, treating juvenile-onset generalized neuroaxonal dystrophy (Hallervorden-Spatz disease), or treating neurodegeneration with brain iron accumulation type-1 (NBIA-1).

Compositions comprising an anti-α-synuclein antibody of the present invention may also be used in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). In certain embodiments, the medicament may further comprise an additional therapeutic agent (e.g., a different anti-α-synuclein antibody).

The invention also provides a method for treating, preventing. or delaying the onset of a synucleinopathy, the method comprising administering to a subject in need thereof an effective amount of a composition comprising an anti-α-synuclein antibody of the present invention, thereby treating, preventing, or delaying the onset of a synucleinopathy in the subject. The invention also provides a method for treating, preventing, or delaying the onset of Parkinson's disease, the method comprising administering to a subject in need thereof an effective amount of a composition comprising an anti-α-synuclein antibody of the present invention, thereby treating, preventing, or delaying the onset of Parkinson's disease in the subject. The invention also provides a method for treating, preventing, or delaying the onset of Parkinson's disease dementia, the method comprising administering to a subject in need thereof an effective amount of a composition comprising an anti-α-synuclein antibody of the present invention, thereby treating, preventing, or delaying the onset of Parkinson's disease dementia in the subject. The invention also provides a method for treating, preventing, or delaying the onset of dementia with Lewy bodies, the method comprising administering to a subject in need thereof an effective amount of a composition comprising an anti-α-synuclein antibody of the present invention, thereby treating, preventing, or delaying the onset of dementia with Lewy bodies in the subject. The invention also provides a method for treating, preventing, or delaying the onset of Lewy body disease, the method comprising administering to a subject in need thereof an effective amount of a composition comprising an anti-α-synuclein antibody of the present invention, thereby treating, preventing, or delaying the onset of Lewy body disease in the subject. The invention also provides a method for treating, preventing, or delaying the onset of juvenile-onset generalized neuroaxonal dystrophy (Hallervorden-Spatz disease), the method comprising administering to a subject in need thereof an effective amount of a composition comprising an anti-α-synuclein antibody of the present invention, thereby treating, preventing, or delaying the onset of juvenile-onset generalized neuroaxonal dystrophy (Hallervorden-Spatz disease) in the subject. The invention also provides a method for treating, preventing, or delaying the onset of multiple system atrophy, the method comprising administering to a subject in need thereof an effective amount of a composition comprising an anti-α-synuclein antibody of the present invention, thereby treating, preventing, or delaying the onset of multiple system atrophy in the subject. The invention also provides a method for treating, preventing, or delaying the onset of pure autonomic failure, the method comprising administering to a subject in need thereof an effective amount of a composition comprising an anti-α-synuclein antibody of the present invention, thereby treating, preventing, or delaying the onset of pure autonomic failure in the subject. The invention also provides a method for treating, preventing, or delaying the onset of neurodegeneration with brain iron accumulation type-1 (NBIA-1), the method comprising administering to a subject in need thereof an effective amount of a composition comprising an anti-α-synuclein antibody of the present invention, thereby treating, preventing, or delaying the onset of neurodegeneration with brain iron accumulation type-1 (NBIA-1) in the subject. In certain embodiments, in any of the above methods, the method further comprises administering to the subject an effective amount of an additional therapeutic agent. In some embodiments, the additional therapeutic agent is another anti-α-synuclein antibody.

In another aspect, the present invention provides an anti-α-synuclein antibody for use in a method for treating, preventing, or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1.

In another aspect, the present invention provides for the use of an anti-α-synuclein antibody in the manufacture of a medicament for treating, preventing, or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1.

In another aspect, the invention provides use of a nucleic acid of the invention in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1).

In certain embodiments, the medicament may further comprise an additional therapeutic agent (e.g., a different anti-α-synuclein antibody).

In another aspect, the invention provides use of an expression vector of the invention in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). In certain embodiments, the medicament may further comprise an additional therapeutic agent (e.g., a different anti-α-synuclein antibody).

In another aspect, the invention provides use of a host cell of the invention in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). In certain embodiments, the medicament may further comprise an additional therapeutic agent (e.g., a different anti-α-synuclein antibody).

In another aspect, the invention provides use of an article of manufacture of the invention in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). In certain embodiments, the medicament may further comprise an additional therapeutic agent (e.g., a different anti-α-synuclein antibody).

In another aspect, the invention provides use of a kit of the invention in the manufacture of a medicament. The medicament may be for use in the treatment, prevention, or for delaying the onset of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). In certain embodiments, the medicament may further comprise an additional therapeutic agent (e.g., a different anti-α-synuclein antibody).

In some embodiments, an anti-α-synuclein antibody of the present invention is a monoclonal antibody. In some embodiments, an anti-α-synuclein antibody of the present invention is a mouse antibody. In other embodiments, an anti-α-synuclein antibody of the present invention is a human, humanized, or chimeric antibody. In particular embodiments, an anti-α-synuclein antibody of the present invention is a human, humanized, or chimeric antibody.

In some embodiments, an anti-α-synuclein antibody of the present invention binds monomeric α-synuclein protein. In other embodiments, an anti-α-synuclein antibody of the present invention binds oligomers (e.g., oligomeric forms) of α-synuclein. In other embodiments, an anti-α-synuclein antibody of the present invention binds aggregated α-synuclein. In yet other embodiments, an anti-α-synuclein antibody of the present invention binds monomeric and oligomeric forms of α-synuclein.

In some embodiments, the present invention provides an anti-α-synuclein antibody for use in the detection of α-synuclein, for use in the detection of monomers of α-synuclein, and/or for use in the detection of oligomers of α-synuclein. In some embodiments, the present invention provides an anti-α-synuclein antibody for use in the detection of α-synuclein fibrils (e.g., fibrillar forms of α-synuclein) or aggragated forms of α-synuclein. In yet other embodiments, an anti-α-synuclein antibody of the present invention is for use in the detection of α-synuclein protein associated with disease or disorder, including, for example, synucleinopathies, Parkinson's disease (PD), Parkinson's disease dementia (PDD), Lewy body disease (LBD), dementia with Lewy bodies (DLB), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1). The detection can be in vitro, in vivo, or in situ.

In some embodiments, the present invention provides a method for diagnosing a synucleinopathic disease or disorder in a subject, comprising assessing the level, localization, conformation, or a combination thereof of α-synuclein in a subject to be diagnosed using an anti-α-synuclein antibody or fragment thereof of the present invention and comparing the level, localization, conformation, or combination thereof of α-synuclein in the subject to one or more reference standards derived from one or more control subjects, where a difference or similarity between the level, localization, conformation, or combination thereof of α-synuclein in the subject and the reference standard indicates whether the subject has a synucleinopathic disease or disorder.

BRIEF DESCRIPTION OF THE FIGURES

FIG. 1 sets forth the amino acid sequence of human α-synuclein (SEQ ID NO:1).

FIGS. 2A and 2B set forth the amino acid sequence of the light chain variable region (SEQ ID NO:2) and of the heavy chain variable region (SEQ ID NO:3), respectively, of anti-α-synuclein monoclonal antibody 1F7.

FIGS. 3A and 3B set forth the amino acid sequence of the light chain variable region (SEQ ID NO:4) and of the heavy chain variable region (SEQ ID NO:5), respectively, of anti-α-synuclein monoclonal antibody 13F3.

DETAILED DESCRIPTION OF EMBODIMENTS OF THE INVENTION

I. Definitions

Figures 4, 6A, 6B:
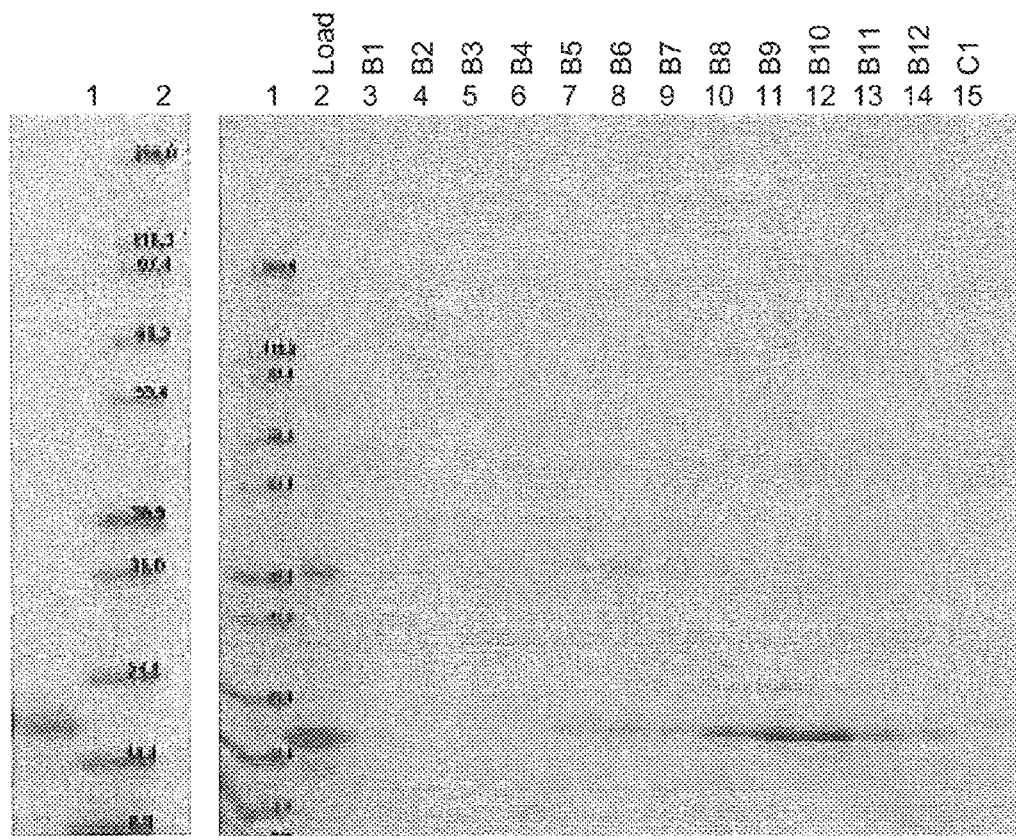
FIG. 4 sets forth the amino acid sequences of the heavy chain and light chain hypervariable regions of anti-α-synuclein monoclonal antibody 1F7 and anti-α-synuclein monoclonal antibody 13F3.
FIGS. 6A and 6B show SDS-PAGE analysis of recombinant human α-synuclein monomer preparation and α-synuclein oligomer preparation, respectively.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-α-synuclein antibody" and "an antibody that binds to α-synuclein" refer to an antibody that is capable of binding α-synuclein with sufficient affinity such that the antibody is useful as a diagnostic and/or therapeutic agent in targeting α-synuclein. In one embodiment, the extent of binding of an anti-α-synuclein antibody to an unrelated, non-α-synuclein protein is less than about 10% of the binding of the antibody to α-synuclein as measured, e.g., by a radioimmunoassay (RIA). In certain embodiments, an antibody that binds to α-synuclein has a dissociation constant (Kd) of ≤1µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-α-synuclein antibody binds to an epitope of α-synuclein that is conserved among α-synuclein from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR amino acid residues of representative anti-α-synuclein antibodies of the present invention comprise those identified in FIG. 4.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-α-synuclein antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "α-synuclein," as used herein, refers to any native α-synuclein from any vertebrate source, including mammals such as primates (e.g. humans) and rodents (e.g., mice and rats), unless otherwise indicated. The term encompasses "full-length," unprocessed α-synuclein as well as any form of α-synuclein that results from processing in the cell or outside of the cell, including phosphorylated forms of α-synuclein. The term also encompasses naturally occurring variants of α-synuclein, e.g., splice variants or allelic variants. The amino acid sequence of an exemplary human α-synuclein is shown in FIG. 1 (SEQ ID NO:1).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease (e.g., delay the onset of) or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-α-synuclein antibodies, and uses thereof. In certain embodiments, antibodies that bind to human α-synuclein are provided. Antibodies of the invention are useful, e.g., for the diagnosis, treatment, and/or prevention of a synucleinopathy, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1).

A. Exemplary Anti-α-Synuclein Antibodies

In one aspect, the invention provides isolated antibodies that bind to α-synuclein. In certain embodiments, an anti-α-synuclein antibody of the present invention binds monomeric α-synuclein; binds oligomeric α-synuclein; binds aggregated α-synuclein; binds to an epitope within amino acid residues 5-78 of human α-synuclein; binds to an epitope within amino acid residues 5-43 of human α-synuclein; binds amino acid residues 5, 8-9, 15-22, 28, 39-43, and 78 of human α-synuclein; binds amino acid residues 5, 8-9, 15-22, 28, and 39-43 of human α-synuclein; binds to an epitope within amino acid residues 37-51 of human α-synuclein; binds to an epitope within amino acid residues 104-118 of human α-synuclein; binds amino acid residues 104-105, 107, 109-111, 113-116, and 118 of human α-synuclein.

In one aspect, the invention provides an anti-α-synuclein antibody comprising at least one, two, three, four, five, or six HVRs selected from (a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:6; (e) HVR-L2 comprising the amino acid sequence of SEQ ID NO:7; and (f) HVR-L3 comprising the amino acid sequence of SEQ ID NO:8.

In one aspect, the invention provides an anti-α-synuclein antibody comprising at least one, two, three, four, five, or six HVRs selected from (a) HVR-H1 comprising the amino acid sequence of SEQ ID NO:15; (b) HVR-H2 comprising the amino acid sequence of SEQ ID NO:16; (c) HVR-H3 comprising the amino acid sequence of SEQ ID NO:17; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.

In one aspect, the invention provides an anti-α-synuclein antibody comprising at least one, at least two, or all three VH HVR sequences selected from (a) HVR-H1 comprising the amino acid sequence of SEQ ID NO:9; (b) HVR-H2 comprising the amino acid sequence of SEQ ID NO:10; and (c) HVR-H3 comprising the amino acid sequence of SEQ ID NO:11. In a further embodiment, the antibody comprises (a) HVR-H1 comprising the amino acid sequence of SEQ ID NO:9; (b) HVR-H2 comprising the amino acid sequence of SEQ ID NO:10; and (c) HVR-H3 comprising the amino acid sequence of SEQ ID NO:11.

In another aspect, the invention provides an anti-α-synuclein antibody comprising at least one, at least two, or all three VL HVR sequences selected from (a) HVR-L1 comprising the amino acid sequence of SEQ ID NO:6; (b) HVR-L2 comprising the amino acid sequence of SEQ ID NO:7; and (c) HVR-L3 comprising the amino acid sequence of SEQ ID NO:8. In one embodiment, the antibody comprises (a) HVR-L1 comprising the amino acid sequence of SEQ ID NO:6; (b) HVR-L2 comprising the amino acid sequence of SEQ ID NO:7; and (c) HVR-L3 comprising the amino acid sequence of SEQ ID NO:8.

In one aspect, the invention provides an anti-α-synuclein antibody comprising at least one, at least two, or all three VH HVR sequences selected from (a) HVR-H1 comprising the amino acid sequence of SEQ ID NO:15; (b) HVR-H2 comprising the amino acid sequence of SEQ ID NO:16; and (c) HVR-H3 comprising the amino acid sequence of SEQ ID NO:17. In a further embodiment, the antibody comprises (a) HVR-H1 comprising the amino acid sequence of SEQ ID NO:15; (b) HVR-H2 comprising the amino acid sequence of SEQ ID NO:16; and (c) HVR-H3 comprising the amino acid sequence of SEQ ID NO:17.

In another aspect, the invention provides an anti-α-synuclein antibody comprising at least one, at least two, or all three VL HVR sequences selected from (a) HVR-L1 comprising the amino acid sequence of SEQ ID NO:12; (b) HVR-L2 comprising the amino acid sequence of SEQ ID NO:13; and (c) HVR-L3 comprising the amino acid sequence of SEQ ID NO:14. In one embodiment, the antibody comprises (a) HVR-L1 comprising the amino acid sequence of SEQ ID NO:12; (b) HVR-L2 comprising the amino acid sequence of SEQ ID NO:13; and (c) HVR-L3 comprising the amino acid sequence of SEQ ID NO:14.

In another aspect, an anti-α-synuclein antibody of the invention comprises (a) a VH domain comprising at least one, at least two, or all three VH HVR sequences selected from (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising at least one, at least two, or all three VL HVR sequences selected from (i) HVR-L1 comprising the amino acid sequence of SEQ ID NO:6, (ii) HVR-L2 comprising the amino acid sequence of SEQ ID NO:7, and (c) HVR-L3 comprising the amino acid sequence of SEQ ID NO:8.

In another aspect, an anti-α-synuclein antibody of the invention comprises (a) a VH domain comprising at least one, at least two, or all three VH HVR sequences selected from (i) HVR-H1 comprising the amino acid sequence of SEQ ID NO:15, (ii) HVR-H2 comprising the amino acid sequence of SEQ ID NO:16, and (iii) HVR-H3 comprising an amino acid sequence selected from SEQ ID NO:17; and (b) a VL domain comprising at least one, at least two, or all three VL HVR sequences selected from (i) HVR-L1 comprising the amino acid sequence of SEQ ID NO:12, (ii) HVR-L2 comprising the amino acid sequence of SEQ ID NO:13, and (c) HVR-L3 comprising the amino acid sequence of SEQ ID NO:14.

In another aspect, an anti-α-synuclein antibody is provided, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:3. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-α-synuclein antibody comprising that sequence retains the ability to bind to α-synuclein. In certain embodiments, a total of 1 to 10 amino acids have been substituted, inserted and/or deleted in SEQ ID NO:3. In certain embodiments, substitutions, insertions, or deletions occur in regions outside the HVRs (i.e., in the FRs). Optionally, the anti-α-synuclein antibody comprises the VH sequence in SEQ ID NO:3, including post-translational modifications of that sequence. In a particular embodiment, the VH comprises one, two or three HVRs selected from: (a) HVR-H1 comprising the amino acid sequence of SEQ ID NO:9, (b) HVR-H2 comprising the amino acid sequence of SEQ ID NO:10, and (c) HVR-H3 comprising the amino acid sequence of SEQ ID NO:11.

In another aspect, an anti-α-synuclein antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:2. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-α-synuclein antibody comprising that sequence retains the ability to bind to α-synuclein. In certain embodiments, a total of 1 to 10 amino acids have been substituted, inserted and/or deleted in SEQ ID NO:2. In certain embodiments, the substitutions, insertions, or deletions occur in regions outside the HVRs (i.e., in the FRs). Optionally, the anti-α-synuclein antibody comprises the VL sequence in SEQ ID NO:2, including post-translational modifications of that sequence. In a particular embodiment, the VL comprises one, two or three HVRs selected from (a) HVR-L1 comprising the amino acid sequence of SEQ ID NO:6; (b) HVR-L2 comprising the amino acid sequence of SEQ ID NO:7; and (c) HVR-L3 comprising the amino acid sequence of SEQ ID NO:8.

In another aspect, an anti-α-synuclein antibody is provided, wherein the antibody comprises a VH as in any of the embodiments provided above, and a VL as in any of the embodiments provided above. In one embodiment, the antibody comprises the VH and VL sequences in SEQ ID NO:3 and SEQ ID NO:2, respectively, including post-translational modifications of those sequences.

In another aspect, an anti-α-synuclein antibody is provided, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-α-synuclein antibody comprising that sequence retains the ability to bind to α-synuclein. In certain embodiments, a total of 1 to 10 amino acids have been substituted, inserted and/or deleted in SEQ ID NO:5. In certain embodiments, substitutions, insertions, or deletions occur in regions outside the HVRs (i.e., in the FRs). Optionally, the anti-α-synuclein antibody comprises the VH sequence in SEQ ID NO:5, including post-translational modifications of that sequence. In a particular embodiment, the VH comprises one, two or three HVRs selected from: (a) HVR-H1 comprising the amino acid sequence of SEQ ID NO:15, (b) HVR-H2 comprising the amino acid sequence of SEQ ID NO:16, and (c) HVR-H3 comprising the amino acid sequence of SEQ ID NO:17.

In another aspect, an anti-α-synuclein antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:4. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-α-synuclein antibody comprising that sequence retains the ability to bind to α-synuclein. In certain embodiments, a total of 1 to 10 amino acids have been substituted, inserted and/or deleted in SEQ ID NO:4. In certain embodiments, the substitutions, insertions, or deletions occur in regions outside the HVRs (i.e., in the FRs). Optionally, the anti-α-synuclein antibody comprises the VL sequence in SEQ ID NO:4, including post-translational modifications of that sequence. In a particular embodiment, the VL comprises one, two or three HVRs selected from (a) HVR-L1 comprising the amino acid sequence of SEQ ID NO:12; (b) HVR-L2 comprising the amino acid sequence of SEQ ID NO:13; and (c) HVR-L3 comprising the amino acid sequence of SEQ ID NO:14.

In another aspect, an anti-α-synuclein antibody is provided, wherein the antibody comprises a VH as in any of the embodiments provided above, and a VL as in any of the embodiments provided above. In one embodiment, the antibody comprises the VH and VL sequences in SEQ ID NO:5 and SEQ ID NO:4, respectively, including post-translational modifications of those sequences.

In a further aspect, the invention provides an antibody that binds to the same epitope in human α-synuclein as an anti-α-synuclein antibody provided herein. For example, in certain embodiments, an antibody is provided that binds to the same epitope as an anti-α-synuclein antibody comprising a VH sequence of SEQ ID NO:3 and a VL sequence of SEQ ID NO:2. In other embodiments, an antibody is provided that competes for binding to human α-synuclein with an anti-α-synuclein antibody comprising a VH sequence of SEQ ID NO:3 and a VL sequence of SEQ ID NO:2. In certain embodiments, an antibody is provided that binds to an epitope within a fragment or region of human α-synuclein comprising amino acid residues 5-43 of SEQ ID NO:1. In certain embodiments, an antibody is provided that binds to an epitope within a fragment or region of human α-synuclein comprising amino acid residues 5-78 of SEQ ID NO:1. In certain embodiments, an antibody is provided that binds to an epitope within a fragment or region of human α-synuclein comprising amino acid residues 37-51 of SEQ ID NO:1. In certain embodiments, an antibody is provided that binds to amino acid residues 5, 8-9, 15-22, 28, and 39-43 of human α-synuclein. In certain embodiments, an antibody is provided that binds to amino acid residues 5, 8-9, 15-22, 28, 39-43, and 78 of human α-synuclein.

In certain embodiments, the present invention provides an antibody that binds to a region of human α-synuclein comprising the amino acid sequence of SEQ ID NO:18. In other embodiments, the present invention provides an antibody that binds to a region of human α-synuclein comprising the amino acid sequence of SEQ ID NO:19. In other embodiments, the present invention provides an antibody that binds to a region of human α-synuclein comprising the amino acid sequence of SEQ ID NO:20.

In other embodiments, an antibody is provided that binds to the same epitope in human α-synuclein as an anti-α-synuclein antibody comprising a VH sequence of SEQ ID NO:5 and a VL sequence of SEQ ID NO:4. In other embodiments, an antibody is provided that competes for binding to human α-synuclein with an anti-α-synuclein antibody comprising a VH sequence of SEQ ID NO:5 and a VL sequence of SEQ ID NO:4. In certain embodiments, an antibody is provided that binds to an epitope within a fragment or region of human α-synuclein comprising amino acid residues 104-118 of SEQ ID NO:1. In certain embodiments, an antibody is provided that binds amino acid residues 104-105, 107, 109-111, 113-116, 118 of human α-synuclein. In certain embodiments, the present invention provides an antibody that binds to a region of human α-synuclein comprising the amino acid sequence of SEQ ID NO:21.

In a further aspect of the invention, an anti-α-synuclein antibody according to any of the above embodiments is a monoclonal antibody, including a chimeric, a humanized, or a human antibody. In one embodiment, an anti-α-synuclein antibody is an antibody fragment, e.g., a Fv, Fab, Fab', scFv, diabody, or F(ab')$_2$ fragment. In another embodiment, the antibody is a full length antibody, e.g., an intact IgG2a antibody or other antibody class or isotype as defined herein.

In a further aspect, an anti-α-synuclein antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions.

Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937

(2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N. J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N. J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for α-synuclein and the other is for any other antigen. In certain embodiments, bispecific antibodies may bind to two different epitopes of α-synuclein. Bispecific antibodies may also be used to localize cytotoxic agents to cells which express α-synuclein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to α-synuclein as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |

TABLE 1-continued

| Original Residue | Exemplary Substitutions | Preferred Substitutions |
| --- | --- | --- |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-α-synuclein antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-α-synuclein antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-α-synuclein antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N. J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); *MRC* 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-α-synuclein antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, NMR, Biacore, etc.

In another aspect, competition assays may be used to identify an antibody that competes with anti-α-synuclein monoclonal antibody 1F7 or that competes with anti-α-synuclein monoclonal antibody 13F3 for binding to human α-synuclein. In certain embodiments, such a competing antibody binds to the same epitope (e.g., a linear or a conformational epitope) that is bound by anti-α-synuclein monoclonal antibody 1F7 or that is bound by anti-α-synuclein monoclonal antibody 13F3. Detailed exemplary methods for mapping an epitope to which an antibody binds are provided in Morris (1996) "Epitope Mapping Protocols," in *Methods in Molecular Biology vol. 66* (Humana Press, Totowa, N.J.).

In an exemplary competition assay, immobilized α-synuclein is incubated in a solution comprising a first labeled antibody that binds to human α-synuclein (e.g., anti-α-synuclein monoclonal antibody 1F7 or anti-α-synuclein monoclonal antibody 13F3) and a second unlabeled antibody that is being tested for its ability to compete with the first antibody for binding to human α-synuclein. The second antibody may be present in a hybridoma supernatant. As a control, immobilized human α-synuclein is incubated in a solution comprising the first labeled antibody but not the second unlabeled antibody. After incubation under conditions permissive for binding of the first antibody to α-synuclein, excess unbound antibody is removed, and the amount of label associated with immobilized α-synuclein is measured. If the amount of label associated with immobilized α-synuclein is substantially reduced in the test sample relative to the control sample, then that indicates that the second antibody is competing with the first antibody for binding to α-synuclein. See Harlow and Lane (1988) *Antibodies: A Laboratory Manual ch.* 14 (Cold Spring Harbor Laboratory, Cold Spring Harbor, N.Y.).

2. Activity Assays

In one aspect, assays are provided for identifying anti-α-synuclein antibodies thereof having biological activity. Biological activity may include, e.g., inhibiting or reducing α-synuclein oligomer formation, inhibiting or reducing α-synuclein aggregation, inhibiting, reducing, or preventing α-synuclein-associated toxicity. Antibodies having such biological activity in vivo and/or in vitro are also provided.

In certain embodiments, an antibody of the invention is tested for such biological activity.

D. Immunoconjugates

The invention also provides immunoconjugates comprising an anti-α-synuclein antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-α-synuclein antibodies provided herein is useful for detecting the presence of α-synuclein in a biological sample. The term "detecting" as used herein encompasses quantitative or qualitative detection. In certain embodiments, a biological sample comprises a cell or tissue, such as brain tissue, or comprises a biological fluid, such as serum, plasma, cerebrospinal fluid, etc.

In one embodiment, an anti-α-synuclein antibody for use in a method of diagnosis or detection is provided. In a further aspect, a method of detecting the presence of α-synuclein in a biological sample is provided. In certain embodiments, the method comprises contacting the biological sample with an anti-α-synuclein antibody as described herein under conditions permissive for binding of the anti-α-synuclein antibody to α-synuclein, and detecting whether a complex is formed between the anti-α-synuclein antibody and α-synuclein. Such method may be an in vitro or in vivo method. In one embodiment, an anti-α-synuclein antibody is used to select subjects eligible for therapy with an anti-α-synuclein antibody, e.g. where α-synuclein is a biomarker for selection of patients.

Exemplary disorders that may be diagnosed using an antibody of the invention include, for example, synucleinopathies, Parkinson's disease (PD), Parkinson's disease dementia (PDD), dementia with Lewy bodies (DLB), Lewy body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1).

In certain embodiments, labeled anti-α-synuclein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-α-synuclein antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a different anti-α-synuclein antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-α-synuclein antibodies provided herein may be used in therapeutic methods. In one aspect, an anti-α-synuclein antibody for use as a medicament is provided. In further aspects, an anti-α-synuclein antibody for use in treating, preventing, or delaying the onset of a synucleinopathy, Parkinson's disease (PD), Parkinson's disease dementia (PDD), dementia with Lewy bodies (DLB), Lew body disease (LBD), juvenile-onset generalized neuroaxonal dystrophy (Hallervorden-Spatz disease), multiple system atrophy (MSA), pure autonomic failure (PAF), and neurodegeneration with brain iron accumulation type-1 (NBIA-1) is provided.

In certain embodiments, an anti-α-synuclein antibody for use in a method of treatment is provided. In certain embodiments, the invention provides an anti-α-synuclein antibody for use in a method of treating an individual having a synucleinopathy, Parkinson's disease (PD), Parkinson's disease dementia (PDD), Lewy body disease (LBD), dementia with Lewy bodies (DLB), juvenile-onset generalized neuroaxonal dystrophy (Hallervorden-Spatz disease), multiple system atrophy (MSA), pure autonomic failure (PAF), or neurodegeneration with brain iron accumulation type-1 (NBIA-1) comprising administering to the individual an effective amount of the anti-α-synuclein antibody. In one such embodiment, the method further comprises administering to the individual an effective amount of at least one additional therapeutic agent, e.g., as described herein. In further embodiments, the invention provides an anti-α-synuclein antibody for use in preventing or reducing aggregation and/or oligomerization of α-synuclein. In certain embodiments, the invention provides an anti-α-synuclein antibody for use in a method of preventing or reducing aggregation and/or oligomerization of α-synuclein in an individual comprising administering to the individual an effective of the anti-α-synuclein antibody to prevent or reduce aggregation and/or oligomerization of α-synuclein. An "individual" according to any of the above embodiments is preferably a human.

In a further aspect, the invention provides for the use of an anti-α-synuclein antibody in the manufacture or preparation of a medicament. In one embodiment, the medicament is for treatment, prevention, or delaying the onset of a synucleinopathy. In another embodiment, the medicament is for treatment, prevention, or delaying the onset of Parkinson's disease. In another embodiment, the medicament is for treatment, prevention, or delaying the onset of Lewy body disease. In another embodiment, the medicament is for treatment, prevention, or delaying the onset of dementia with Lewy bodies. In another embodiment, the medicament is for treatment, prevention, or delaying the onset of juvenile-onset generalized neuroaxonal dystrophy (Hallervorden-Spatz disease). In another embodiment, the medicament is for treatment, prevention, or delaying the onset of multiple system atrophy (MSA). In another embodiment, the medicament is for treatment, prevention, or delaying the onset of pure autonomic failure (PAF). In another embodiment, the medicament is for treatment or prevention of neurodegeneration with brain iron accumulation type-1 (NBIA-1).

In a further embodiment, the medicament is for use in a method of treating, preventing, or delaying the onset of a synucleinopathy comprising administering to an individual having a synucleinopathy an effective amount of the medicament. In a further embodiment, the medicament is for use in a method of treating, preventing, or delaying the onset of Parkinson's Disease comprising administering to an individual having Parkinson's Disease an effective amount of the medicament. In a further embodiment, the medicament is for use in a method of treating, preventing, or delaying the onset of Parkinson's disease dementia comprising administering to an individual having Parkinson's disease dementia an effective amount of the medicament. In a further embodiment, the medicament is for use in a method of treating, preventing, or delaying the onset of juvenile-onset generalized neuroaxonal dystrophy (Hallervorden-Spatz disease) comprising administering to an individual having juvenile-onset generalized neuroaxonal dystrophy (Hallervorden-Spatz disease) an effective amount of the medicament. In a further embodiment, the medicament is for use in a method of treating, preventing, or delaying the onset of Lewy body disease comprising administering to an individual having Lewy body disease an effective amount of the medicament. In a further embodiment, the medicament is for use in a method of treating, preventing, or delaying the onset of dementia with Lewy bodies comprising administering to an individual having dementia with Lewy bodies an effective amount of the medicament. In a further embodiment, the medicament is for use in a method of treating, preventing, or delaying the onset of multiple system atrophy comprising administering to an individual having multiple system atrophy an effective amount of the medicament. In a further embodiment, the medicament is for use in a method of treating, preventing, or delaying the onset of pure autonomic failure comprising administering to an individual having pure autonomic failure an effective amount of the medicament. In a further embodiment, the medicament is for use in a method of treating, preventing, or delaying the onset of neurodegeneration with brain iron accumulation type-1 comprising administering to an individual having neurodegeneration with brain iron accumulation type-1 an effective amount of the medicament. In certain embodiments, any one of the above methods further comprises administering to the individual an effective amount of at least one additional therapeutic agent, e.g., as described herein.

In some aspects, the medicament is for reducing the levels of α-synuclein protein (e.g., reducing α-synuclein monomers, reducing α-synuclein oligomers, reducing α-synuclein multimers, reducing α-synuclein fibrils, reducing α-synuclein aggregates). In a further embodiment, the medicament is for use in a method of reducing the levels of α-synuclein protein (e.g., reducing α-synuclein monomers, reducing α-synuclein oligomers, reducing α-synuclein multimers, reducing α-synuclein fibrils, reducing α-synuclein aggregates) in an individual comprising administering to the individual an amount effective of the medicament to reduce the levels of α-synuclein protein (e.g., reduce α-synuclein monomers, reduce α-synuclein oligomers, reduce α-synuclein multimers, reduce α-synuclein fibrils, reducing α-synuclein aggregates). An "individual" according to any of the above embodiments may be a human.

In a further aspect, the invention provides a method for treating, preventing, or delaying the onset of a synucleinopathy. In one embodiment, the method comprises administering to an individual having a synucleinopathy an effective amount of an anti-α-synuclein antibody. In another aspect, the invention provides a method for treating, preventing, or delaying the onset of Parkinson's Disease. In one embodiment, the method comprises administering to an individual having Parkinson's Disease an effective amount of an anti-α-synuclein antibody. In another aspect, the invention provides a method for treating, preventing, or delaying the onset of Lewy body disease. In one embodiment, the method comprises administering to an individual having Lewy body disease an effective amount of an anti-α-synuclein antibody. In another aspect, the invention provides a method for treating, preventing, or delaying the onset of dementia with Lewy bodies. In one embodiment, the method comprises administering to an individual having dementia with Lewy bodies an effective amount of an anti-α-synuclein antibody. In yet another aspect, the invention provides a method for treating, preventing, or delaying the onset of multiple system atrophy. In one embodiment, the method comprises administering to an individual having multiple system atrophy an effective amount of an anti-α-synuclein antibody. In yet another aspect, the invention provides a method for treating, preventing, or delaying the onset of Parkinson's disease dementia. In one embodiment, the method comprises administering to an individual having Parkinson's disease dementia an effective amount of an anti-α-synuclein antibody. In yet another aspect, the invention provides a method for treating, preventing, or delaying the onset of juvenile-onset generalized neuroaxonal dystrophy (Hallervorden-Spatz disease). In one embodiment, the method comprises administering to an individual having juvenile-onset generalized neuroaxonal dystrophy (Hallervorden-Spatz disease) an effective amount of an anti-α-synuclein antibody. In yet another aspect, the invention provides a method for treating, preventing, or delaying the onset of pure autonomic failure. In one embodiment, the method comprises administering to an individual having pure autonomic failure an effective amount of an anti-α-synuclein antibody. In yet another aspect, the invention provides a method for treating, preventing, or delaying the onset of neurodegeneration with brain iron accumulation type-1. In one embodiment, the method comprises administering to an individual having neurodegeneration with brain iron accumulation type-1 an effective amount of an anti-α-synuclein antibody. In certain embodiments, any one of the methods above further comprises administering to the individual an effective amount of at least one additional therapeutic agent, as described herein. An "individual" according to any of the above embodiments may be a human.

In a further aspect, the invention provides a method for reducing the levels of α-synuclein protein (e.g., reducing α-synuclein monomers, reducing α-synuclein oligomers, reducing α-synuclein multimers, reducing α-synuclein fibrils, reducing α-synuclein aggregates) in an individual. In one embodiment, the method comprises administering to the individual an effective amount of an anti-α-synuclein antibody to reduce α-synuclein monomers, to reduce α-synuclein oligomers, to reduce α-synuclein multimers, to reduce α-synuclein fibrils, or to reduce α-synuclein aggregates. In one embodiment, an "individual" is a human.

In a further aspect, the invention provides pharmaceutical formulations comprising any of the anti-α-synuclein antibodies provided herein, e.g., for use in any of the above therapeutic methods. In one embodiment, a pharmaceutical formulation comprises any of the anti-α-synuclein antibodies provided herein and a pharmaceutically acceptable carrier. In another embodiment, a pharmaceutical formulation comprises any of the anti-α-synuclein antibodies provided herein and at least one additional therapeutic agent, e.g., as described herein.

Antibodies of the invention can be used either alone or in combination with other agents in a therapy. For instance, an antibody of the invention may be co-administered with at least one additional therapeutic agent. In certain embodiments, an additional therapeutic agent is a different anti-α-synuclein antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-α-synuclein antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention, treatment, or delaying the onset of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-α-synuclein antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-α-synuclein antibody.

III. Examples

The following are examples of methods and compositions of the invention. It is understood that various other embodiments may be practiced, given the general description provided above.

EXAMPLE 1

Production of Recombinant Human α-Synuclein

Recombinant human α-synuclein was expressed in *E. coli* bacterial cells 58F3 transfected with pST239/α-synuclein plasmid which contained nucleic acid encoding human α-synuclein. *E. coli* paste from 1 L shake flask culture (15-20 g pellet) was solubilized in 10 volumes (w/v) of 20 mM Tris-HCl, pH 8.0, containing 7 M guanidine HCl. The cell lysate was centrifuged and the resulting supernatant was loaded onto a 20-ml Qiagen Ni-NTA metal chelate column equilibrated in 20 mM Tris-HCl, pH 8.6, containing 6 M guanidine HCl. The column was washed with additional buffer containing 50 mM imidazole (Ultrol grade; Calbiochem). The protein was eluted with buffer containing 250 mM imidazole. After dialysis, the N-terminal Unizyme-polyhis tag was cleaved off according to the manufacturer's (Qiagen) instructions. The detagged protein was subsequently dialyzed into 6 M guanidine hydrochloride, pH 6.0.

To generate recombinant human α-synuclein monomer, the α-synuclein protein was dialyzed into PBS (8 mM $Na_2HPO_4$, 137 mM NaCl, 2 mM $KH_2PO_4$, 2.7 mM KCl, pH 7.4) and then filtered through 0.2 μm filter (Millipore). To generate recombinant human α-synuclein soluble oligomers, the dialyzed monomeric recombinant human α-synuclein protein was further concentrated to 50 uM and incubated with docosahexaenoic acid (DHA, Sigma) in a 1:50 molar ratio (α-synuclein to DHA) at 37° C., 500 RPM, for 2 hours using a thermomixer (Eppendorf). The entire mixture was subsequently purified over a Superdex 75 10/300 GL (GE) column pre-equilibrated with 20 mM Tris-HCl, pH 7.5, 150 mM NaCl. Based on SDS-PAGE gel analysis, fractions containing the oligomers were subsequently pooled. Purified α-synuclein monomers and α-synuclein oligomers were separately used as antigens to generate antibodies.

Figure 5:
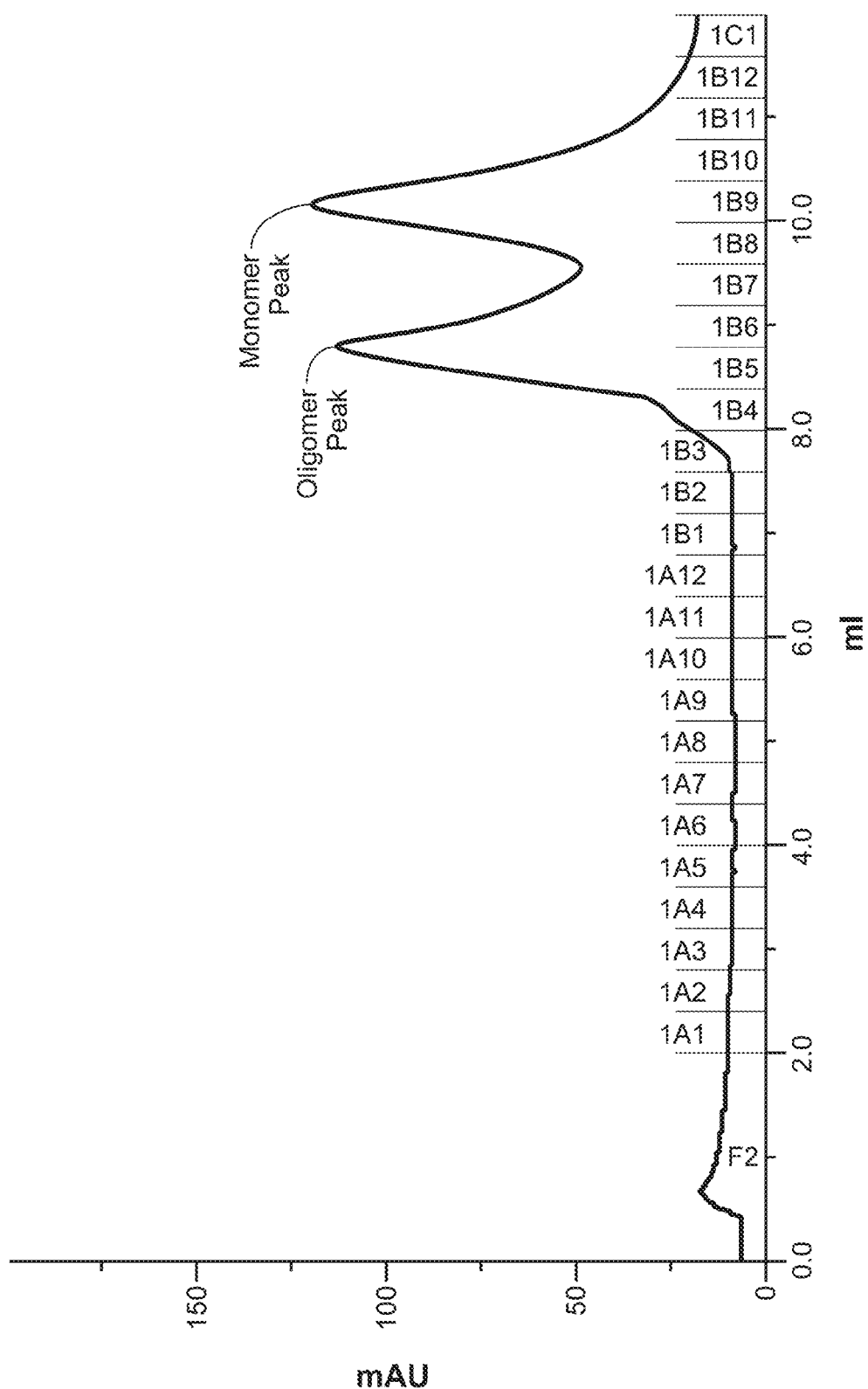
FIG. 5 shows gel filtration chromatogram of recombinant human α-synuclein oligomers separated on a Superdex 75 10/300 GL column.

FIG. 5 shows gel filtration chromatogram of recombinant human α-synuclein oligomer separated as described above on a Superdex 75 10/300 column. FIG. 6A and FIG. 6B show SDS-PAGE analysis of α-synuclein monomer (FIG. 6A) and α-synuclein oligomers (FIG. 6B) on a 20% Tris-slycine gel stained with coomassie blue. The α-synuclein oligomers were prepared as described above and separated on a Superdex 75 10/300 GL column. Column fractions corresponding to lanes 7-9 (oligomeric form) were subsequently pooled and used for antibody generation as described herein.

EXAMPLE 2

Development and Characterization of Mouse Monoclonal Anti-α-Synuclein Antibodies Alpha-synuclein knock-out mice (JAX003692, Jackson Laboratory, Bar Harbor, Me.) were immunized twice weekly via i.p. and/or footpad injection with 2-10 μg each of human α-synuclein monomeric or oligomeric protein (prepared as described above) for a total of 8-13 injections. A pre-fusion boost with 2-10 μg of human α-synuclein monomeric or oligomeric proteins via i.p. and/or footpad injection was given three days prior to fusion. Splenocytes and/or lymphocytes from the immunized mice, all of whose sera demonstrated binding to directly coated human and mouse α-synuclein monomeric proteins by ELISA, were fused with X63-Ag8.653 or P3X63-Ag8U.1 mouse myeloma cells (American Type Culture Collection, Manassas, Va.) via electrofusion (Cyto Pulse CEEF-50 apparatus, BTX Harvard Apparatus, Holliston, Mass.). After washing twice with Cytofusion Medium C (BTX Harvard Apparatus 47-0001), the isolated lymphocytes and myeloma cells were mixed at a 1:1 ratio and then resuspended at 10 million cells/ml in Cytofusion Medium C; electrofusion was performed according to manufacturer's guidance. Fused cells were cultured in ClonaCell-HY Medium C (Stemcell Technologies Cat #03803) overnight at 37° C. in a 7% $CO_2$ incubator.

The following day, the fused cells were centrifuged and then suspended in 10 ml ClonaCell-HY Medium C with anti-mouse IgG-FITC (Jackson Immunoresearch, West Grove, Pa.) and then gently mixed with 90 ml Methylcellulose-based ClonaCell-HY Medium D (Stemcell Technologies Cat #03804) containing HAT components. The cells were plated into OmniTray plates (Thermo Fisher Scientific, Rochester, N.Y.) and allowed to grow at 37° C. in a 7% $CO_2$ incubator. After 10 days incubation, fluorescent colonies were selected and transferred into 96-well plates (Becton Dickinson, Cat #353075) containing 200 µL/well ClonaCell-HY Medium E (StemCell Technologies Cat #03805) using a Clonepix FL (Molecular Devices, Sunnyvale, Calif.).

Supernatants from the cells were screened for binding to directly coated human α-synuclein oligomeric and/or human and mouse α-synuclein, β-synuclein, and γ-synuclein monomeric proteins by ELISA, to FFPE or PFA-fixed 293 cells overexpressing α-synuclein, β-synuclein, or γ-synuclein by IHC, and to mouse brain lysates by Western blot. Positive clones were subcloned using the FACSAria II (Becton Dickinson, Franklin Lakes, N.J.), and then expanded for large-scale production in bioreactors (Integra Biosciences, Chur, Switzerland). RNA was extracted from the positive hybridoma cell lines using the RNeasy kit (Qiagen, Hilden, Germany), and cDNA was generated and amplified for sequence determination. Variable region genes of heavy and light chains were inserted into pRK plasmid vectors (Genentech) for expression, and the associated antibody heavy and light chains from unique clones were expressed recombinantly in 293 cells. Supernatants were then purified by Protein A affinity chromatography as previously described. (See Hongo et al., Hybridoma 19:303, 2000.) Two mouse monoclonal antibodies were identified and further characterized, designated anti-α-synuclein monoclonal antibody 1F7 (mIgG2a) and anti-α-synuclein monoclonal antibody 13F3 (mIgG2a).

EXAMPLE 3

Monovalent Affinities of Murine Anti-α-Synuclein Monoclonal Antibodies for Human α-Synuclein Monovalent affinities of anti-α-synuclein antibodies 13F3 and 1F7 for human α-synuclein were assessed using Surface Plasmon Resonance in a Biacore T200 instrument. These experiments utilized an antibody capture format where the test antibody was immobilized by binding the test antibody to a chip pre-coated with a murine IgG capture reagent and subsequently allowed to bind α-synuclein protein in solution.

A murine IgG capture chip was prepared using the GE murine IgG capture kit according to the manufacturer's instructions. Briefly, a Series S CM5 sensor chip was activated with a mixture of EDC/NHS before exposure to a solution of capture antibody in a 10 mM sodium acetate (pH 5.0) buffer. Remaining covalent attachment sites were blocked with ethanolamine.

To assess binding, anti-α-synuclein monoclonal antibody 13F3 and anti-α-synuclein monoclonal antibody 1F7 were captured using a 1 µg/ml solution in running buffer (1×HBSP; 10 mM HEPES, pH 7.4, 150 mM NaCl, 0.05% Tween20) at a flow rate of 10 µl/min. Binding of human α-synuclein in solution was monitored at six different concentrations (a three-fold dilution series spanning concentrations from single-digit nanomolar to greater than 1 µM) and one replicate concentration, at a flow rate of 30 µl/min. The assay was performed at 25° C. with samples diluted in running buffer (1×HBSP); surfaces were regenerated by injection of 10 mM glycine (pH 1.7) at 10 µl/min for 180 seconds. Steady-state analysis was applied to the resulting data. The affinities ($K_D$) of each of these two antibodies to recombinant human α-synuclein are shown below in Table 2.

TABLE 2

| Antibody | $K_D$ (Expt A) | $K_D$ (Expt B) |
|---|---|---|
| 1F7 | 130 nM | 160 nM |
| 13F3 | 410 nM, 490 nM | 460 nM |

Figure 7:
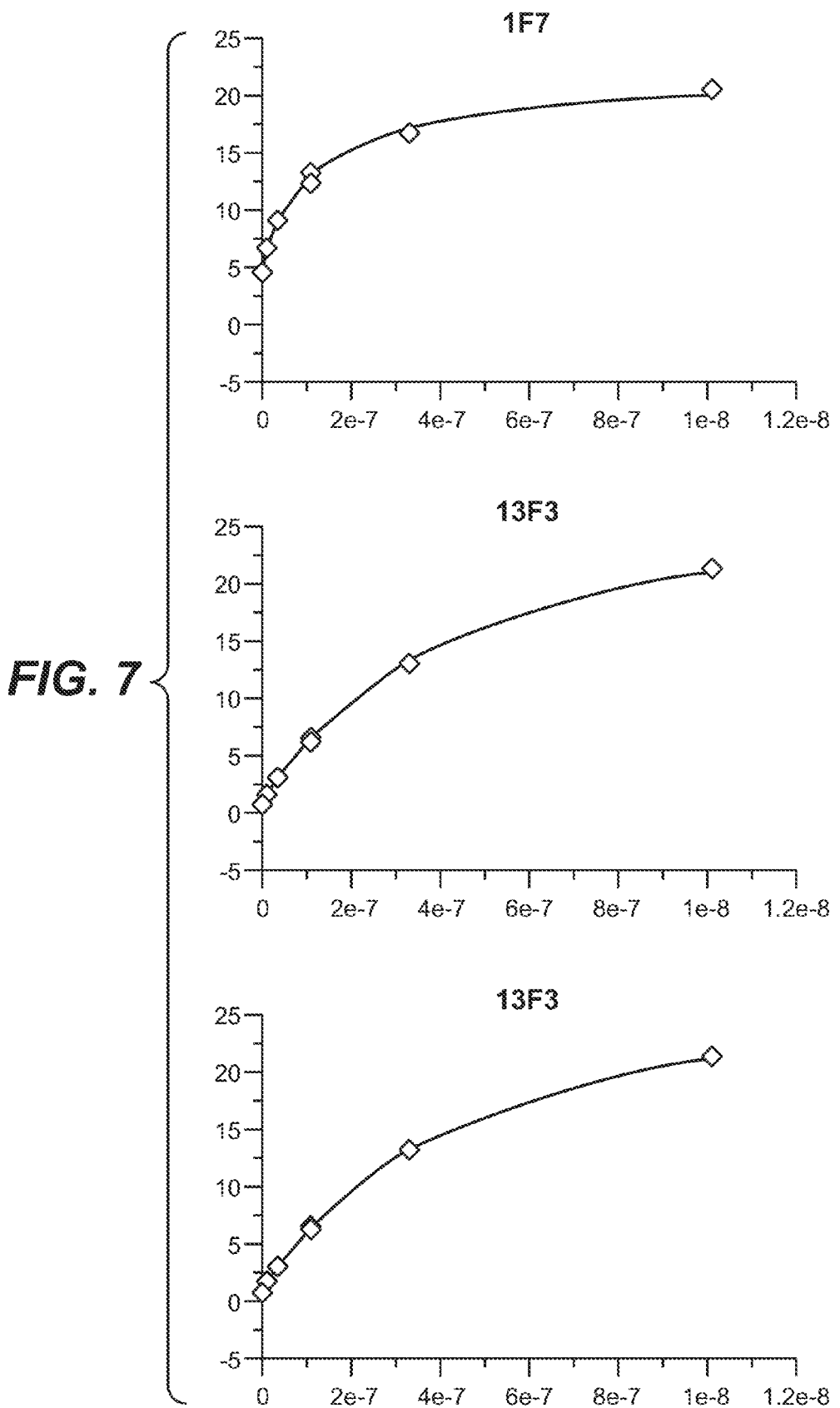
FIG. 7 sets forth data showing binding curves of anti-α-synuclein monoclonal antibody 1F7 and anti-α-synuclein monoclonal antibody 13F3 to recombinant human α-synuclein.

As shown in Table 2 above, monovalent affinities (as measured by equilibrium constants described above) were $4.5\times10^{-7}$ M and $4.7\times10^{-7}$ M for monoclonal antibody 13F3, and $1.3\times10^{-7}$ M and $1.8\times10^{-7}$ M for monoclonal antibody 1F7. FIG. 7 shows graphical representation of the binding curves obtained in the experiments described above (antibody 1F7 top panel, antibody 13F3 two lower panels, antibody concentrations on x-axis, α-synuclein on y-axis).

EXAMPLE 4

Recognition of Different Forms of α-Synuclein

Binding of monoclonal antibody 13F3 and monoclonal antibody 1F7 to different forms of human α-synuclein was investigated using a Biacore chip on which biotinylated human α-synuclein was immobilized via a biotin-neutravidin interaction. To avoid complications due to potential avidity effects, monoclonal antibodies 13F3 and 1F7 were investigated in Fab format. Fabs of each anti-α-synuclein antibody were produced from mIgG2a using proteolytic digestion with immobilized papain (Thermo Scientific) and subsequent purification of the Fab fragments using methods standard in the art.

Neutravidin (Thermo Scientific, Product #31000) was covalently coupled to a Series S CM5 Biacore chip (GE) using the GE Amine Coupling Kit. Briefly, each flow cell in turn was activated with EDC/NHS, exposed to 10 µg/ml Neutravidin in 10 mM sodium acetate (pH 5) for five minutes, and the surface blocked with ethanolamine. This resulted in immobilization of approximately 2200-2600 Response Units (RU) Neutravidin on each of the four flow cells, including the reference cell FC1. Subsequently, biotinylated α-synuclein was immobilized as desired by diluting in running buffer (1×HBSP) to 0.5-2 µg/ml and flowing across the relevant flow cell at 30 µl/min while carefully monitoring the response.

Three forms of recombinant human α-synuclein were assessed in parallel. Recombinant human monomeric α-synuclein biotinylated via a genetically-attached Avi-tag was immobilized on Flow Cell 2 (estimated 28 RU immobilized). Recombinant human oligomeric, avi-tag biotinylated α-synuclein was immobilized on Flow Cell 3 (estimated 22 RU immobilized). Non-avi-tagged recombinant human α-synuclein oligomerized prior to chemical biotinylation with NHS-PEG4-Biotin was immobilized on Flow Cell 4 (estimated 15 RU immobilized).

The chip coated with three forms of biotinylated recombinant human α-synuclein was then allowed to bind a concentration range of monoclonal antibodies 1F7 and 13F3 Fab fragments (six concentrations following a three-fold dilution series from a top concentration of 2 µM; replicate concentration 667 nM assessed twice). Binding was assessed using a flow rate of 30 µl/min and association and dissociation periods of 300 seconds each. Between Fab fragment injections, the surface was regenerated by a 60 second injection of 10 mM glycine (pH 1.7) at 10 µl/min. Each concentration series was followed twice.

Figure 8:
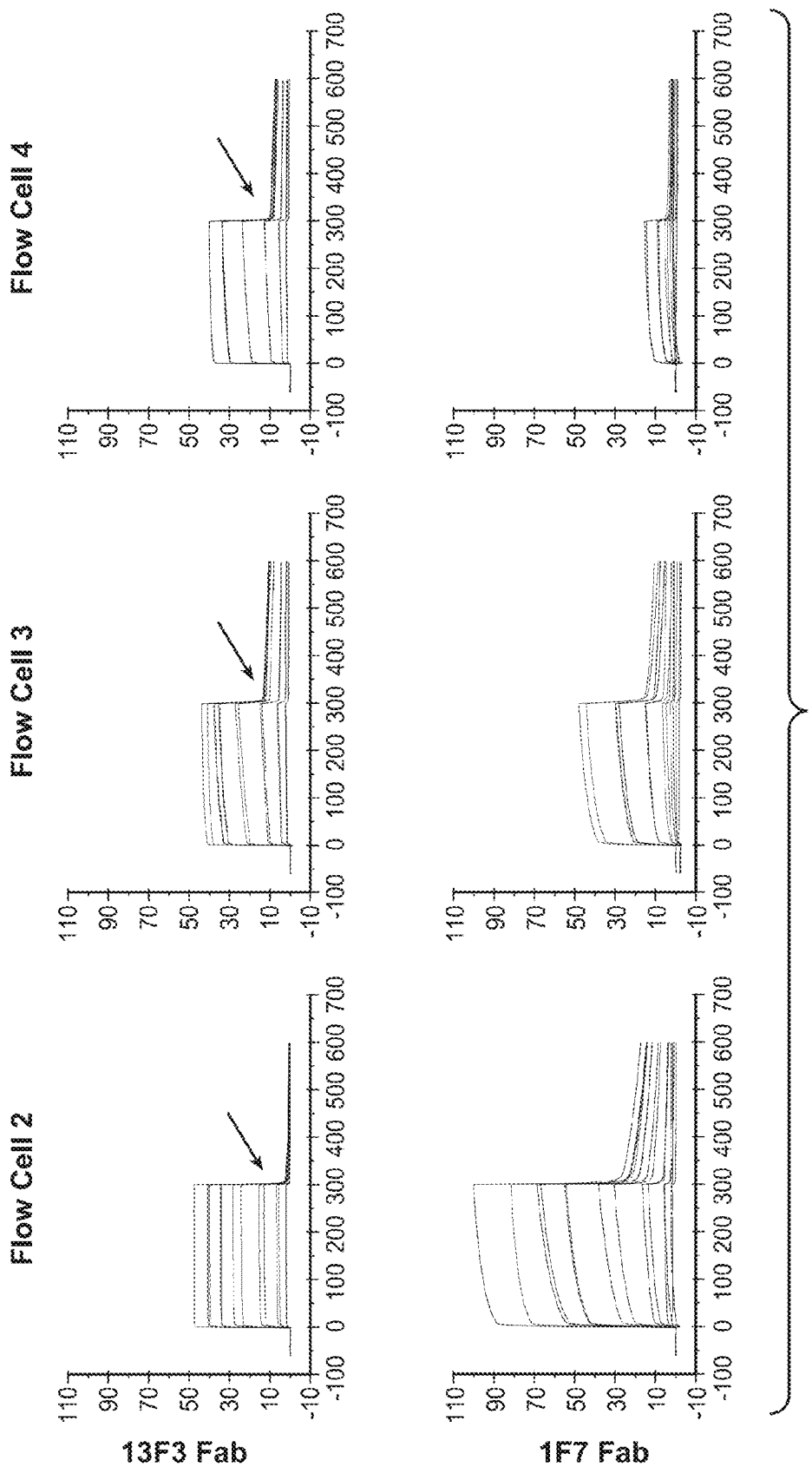
FIG. 8 sets forth data showing binding characteristics of anti-α-synuclein monoclonal antibody 13F3 and anti-α-synuclein monoclonal antibody 1F7 to three different forms of recombinant human α-synuclein.

The results of these analyses are shown in FIG. 8. Monoclonal antibody 13F3 Fab showed rapid kinetics for binding to biotinylated monomeric recombinant human α-synuclein immobilized on Flow Cell 2 ("native" α-synuclein enzymatically biotinylated monomeric α-synuclein). When monoclonal antibody 13F3 was allowed to bind biotinylated oligomeric recombinant human α-synuclein on Flow Cell 3 (enzymatically biotinylated oligomeric α-synuclein) or Flow Cell 4 (chemically biotinylated α-synuclein, that is oligomerized and chemically biotinylated via amine coupling), a binding component displaying much slower dissociation was observed; in addition, a rapidly-dissociating component was also observed. Such binding characteristics were not observed with antibody 1F7.

These results obtained by Biacore analysis showed that monoclonal antibody 13F3 Fab demonstrated multi-modal binding to biotinylated α-synuclein oligomers. Monoclonal antibody 13F3 showed a qualitatively different binding characteristics to monomeric and oligomeric α-synuclein. As antibody Fab fragment interaction with α-synuclein is expected to be monovalent, these results suggested that the enhanced binding to oligomeric α-synuclein is not avidity-mediated, and are consistent with this antibody's recognition of an oligomer-specific epitope, in addition to a monomeric epitope on α-synuclein.

EXAMPLE 5

Identification of a Binding Epitope of Anti-α-Synuclein Monoclonal Antibody 13F3 and of Anti-α-Synuclein Monoclonal Antibody 1F7 by NMR Spectroscopy NMR was used to identify the binding epitope of anti-α-synuclein monoclonal antibody 13F3 and of anti-α-synuclein monoclonal antibody 1F7 as follows. NMR samples were prepared by adding a solution of $^{13}C/^{15}N$ labeled recombinant human α-synuclein in PBS (pH 7.0) at a concentration of 1 mg/ml (71 µM) purchased from Giotto Biotech (Sesto Fiorentino (FI), Italy) to a volume of 180 µl into 3 mm NMR tubes. Complex formation of the antibody bound form of α-synuclein was achieved by addition of an 18 mg/ml (120 µM) solution of antibody 13F3 and 17.8 mg/ml (118 µM) of antibody 1F7 in PBS (pH 7.2) in aliquots of 9 µl to the NMR sample. 2D HSQC-TROSY spectra were recorded at increasing concentration of Fab and the proton-amide cross peak intensity monitored in CCPN. (See Vranken et al (2005) Proteins 59:687-696.) All spectra were recorded at calibrated 300 K on a Bruker 600 MHz spectrometer using a 5 mm TXI cryo-probe. The final molar ratio used for data analysis of 1:0.5 α-synuclein:Fab. All data was processed using Topspin 3.1 (Bruker Karlsruhe, Germany) and visualized and analyzed using CCPN. Samples of $^{13}C/^{15}N$ labeled α-synuclein were measured in PBS (pH 7.2) buffer at 1 mg/ml corresponding to a concentration of 71 µM. The spectra were assigned using the submitted NMR data from the BMRB with the accession number 6968. Triple resonance information from the 3D TROSY-HNCO was used to confirm the published assignments and remove ambiguities for signal overlap. Signal intensities were evaluated in CCPN. The signal errors were extrapolated in CCPN based on the signal to noise of the recorded data.

Figure 9A:
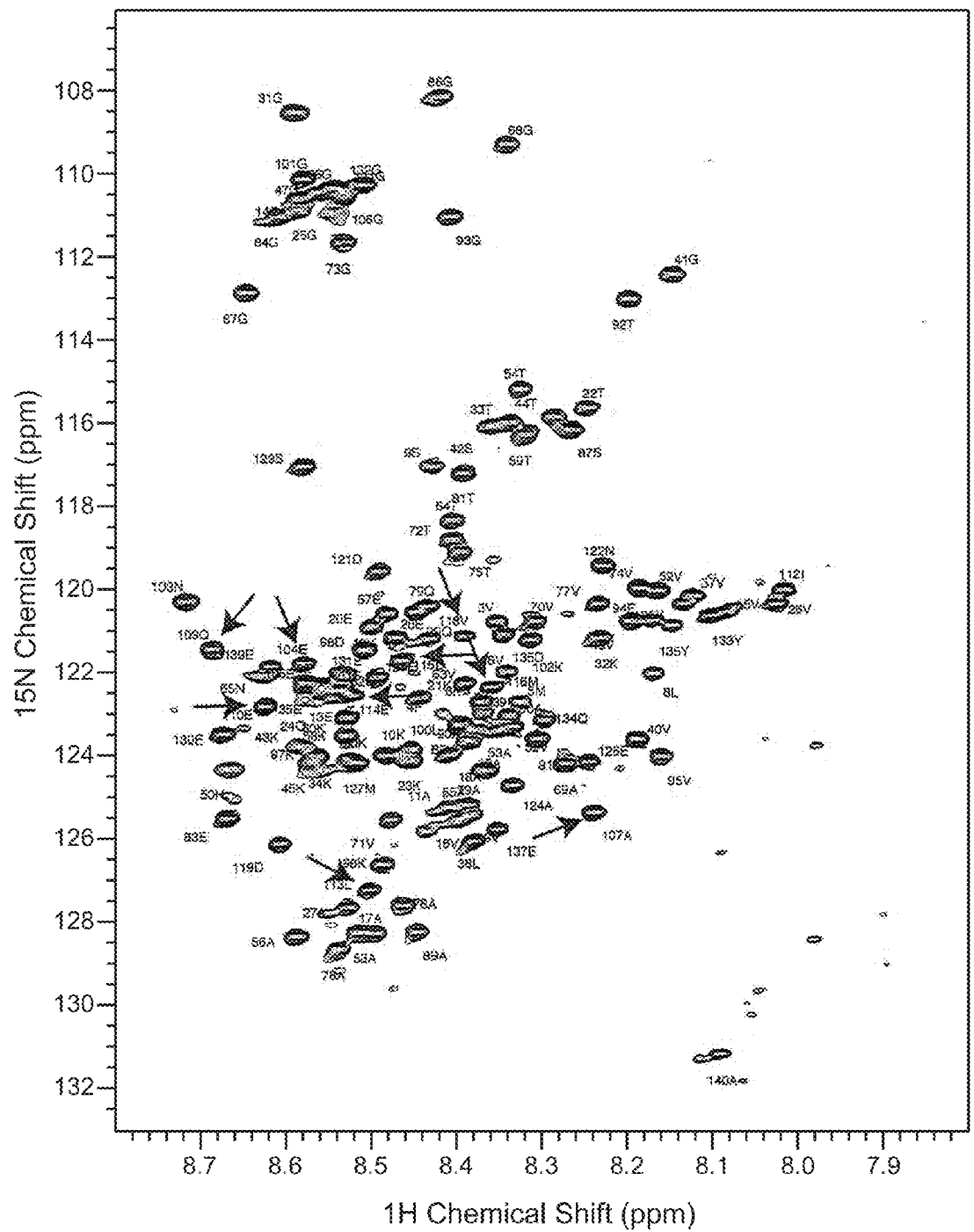
FIGS. 9A and 9B set forth data showing NMR spectra of anti-α-synuclein monoclonal antibody 13F3 Fab binding to recombinant human α-synuclein alone and with a molar ration of 1:0.5, respectively.
Figure 9B:
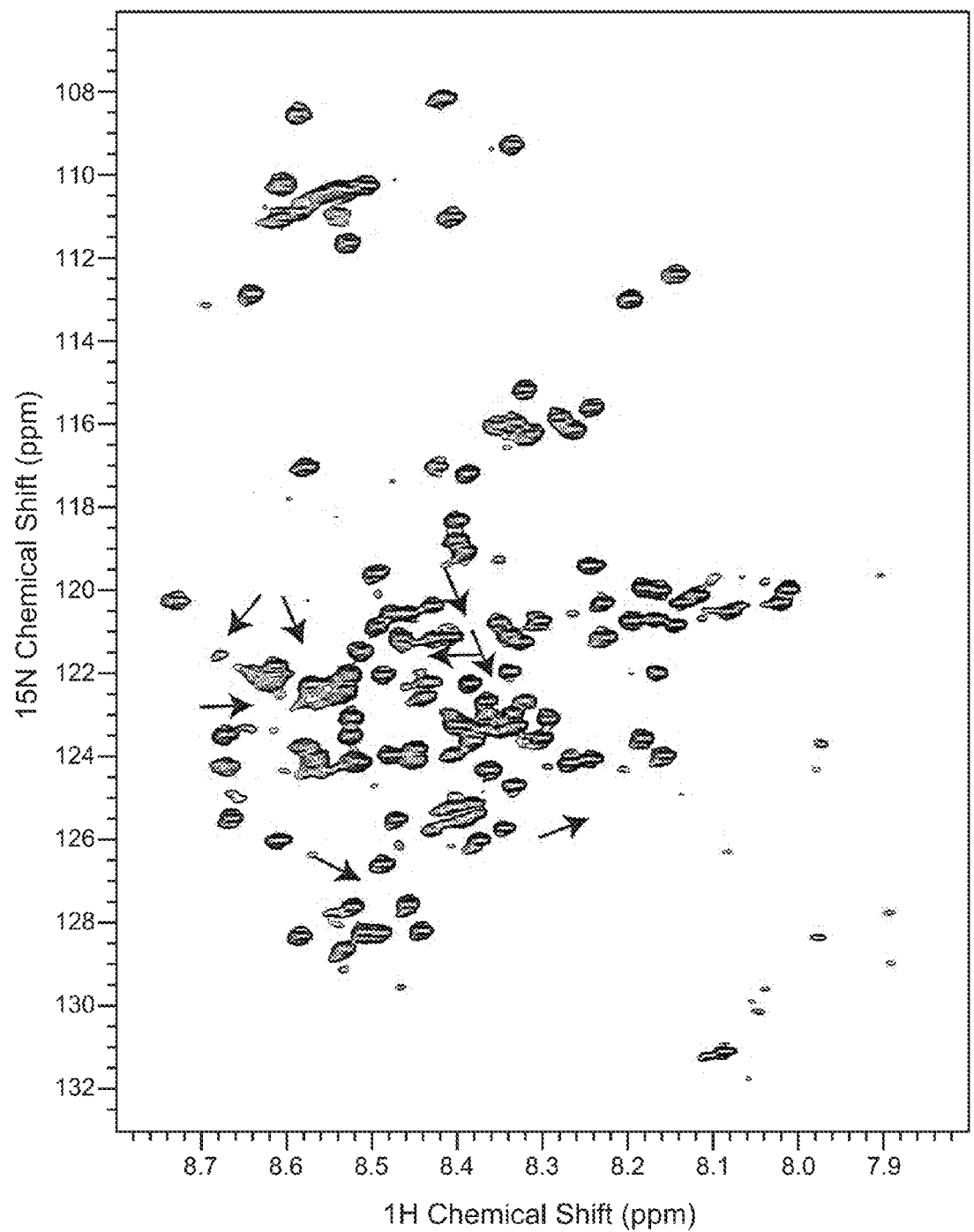

NMR results for the binding of anti-α-synuclein monoclonal antibody 13F3 Fab were as follows. Spectra of recombinant human α-synuclein alone and with a molar ratio of 1:0.5 are shown in FIGS. 9A and 9B, respectively. The binding epitope was identified as the amino acid residue signals with a steep decrease in signal intensity in the complex spectrum. Amino acid residues were classified as belonging to the binding epitope of the antibody by the reduction of the signal in the 2D Heteronuclear Single Quantum Coherence-Transversal Relaxation Optimized Spectroscopy (2D HSQC-TROSY) spectra. (See Pervushin et al (1997) PNAS 94:12366-12371.) A factor of signal intensity attenuation above 50 was used as cutoff. For anti-α-synuclein monoclonal antibody 13F3 Fab amino acid residues 104-105, 107, 109-111, 113-116 and 118 of human α-synuclein meet this criterion. These results showed that monoclonal antibody 13F3 bound amino acid residues 104-105, 107, 109-111, 113-116 and 118 of human α-synuclein, indicating that the binding epitope of monoclonal antibody 13F3 comprises amino acid residues 104-118 of human α-synuclein, and more specifically, comprises amino acid residues 104-105, 107, 109-111, 113-116 and 118 of human α-synuclein. (See Table 3 below.)

Additional to the signal attenuation, chemical shift perturbations were observed for amino acid residues 98-103, 119-122, and 124-125 where observed with anti-α-synuclein monoclonal antibody 13F3 Fab binding to human α-synuclein. These chemical shift perturbations are attributed to indirect effects of Fab binding. Effects of chemical shift perturbation were also observed for histidine 50; these are attributed to secondary effects such as slight pH changes. The signal from glycine 106 is overlapped; proline residues 108 and 117 have no HSQC signature. It is noted that residue isoleucine 112 is not as strongly affected, with a signal attenuation of 1.79.

Figure 10A:
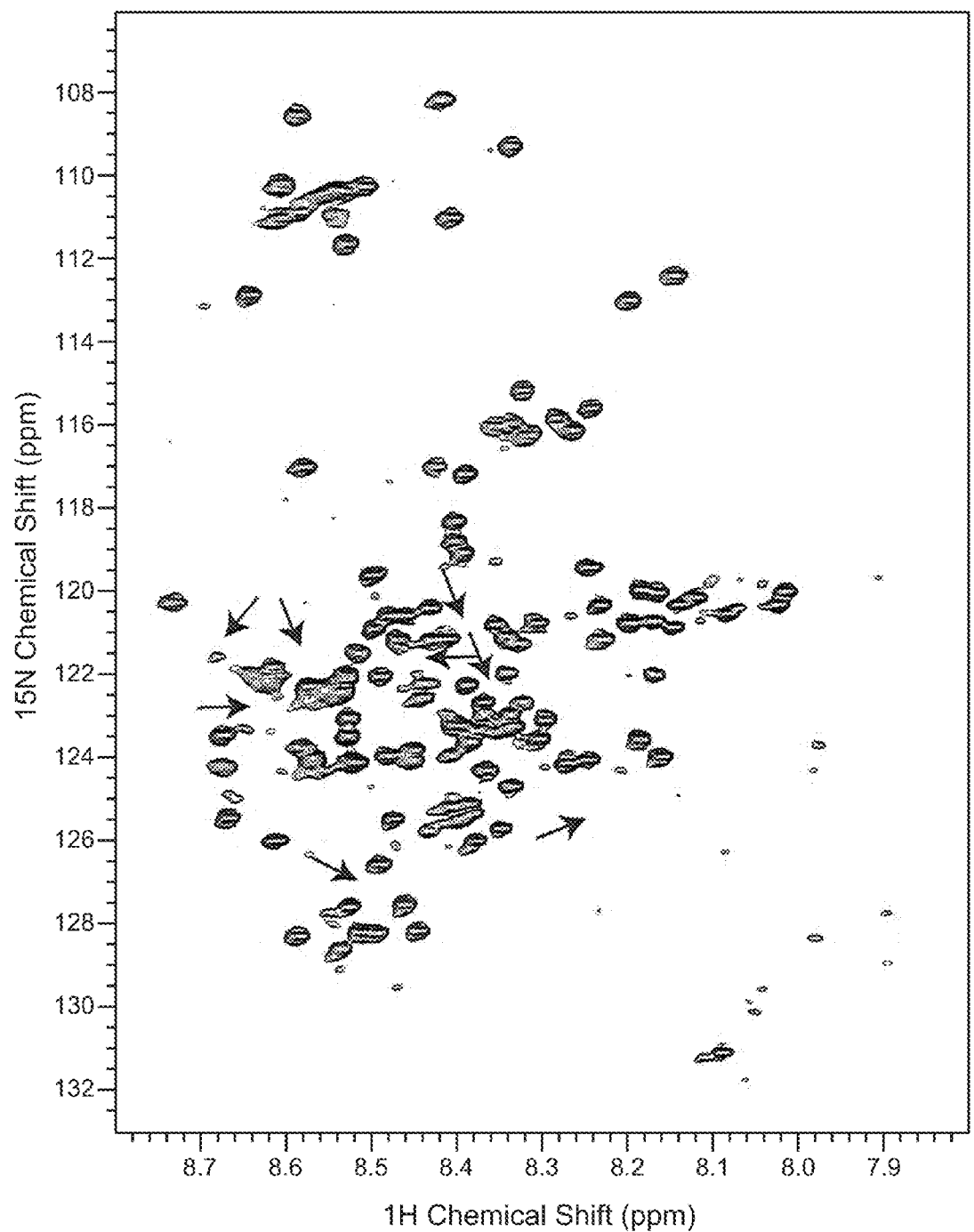
FIGS. 10A and 10B set forth data showing NMR spectra of anti-α-synuclein monoclonal antibody 13F3 Fab binding to recombinant human α-synuclein alone or in combination with a synthetic peptide of human α-synuclein (amino acid residues 105-123 of human α-synuclein), respectively.
Figure 10B:
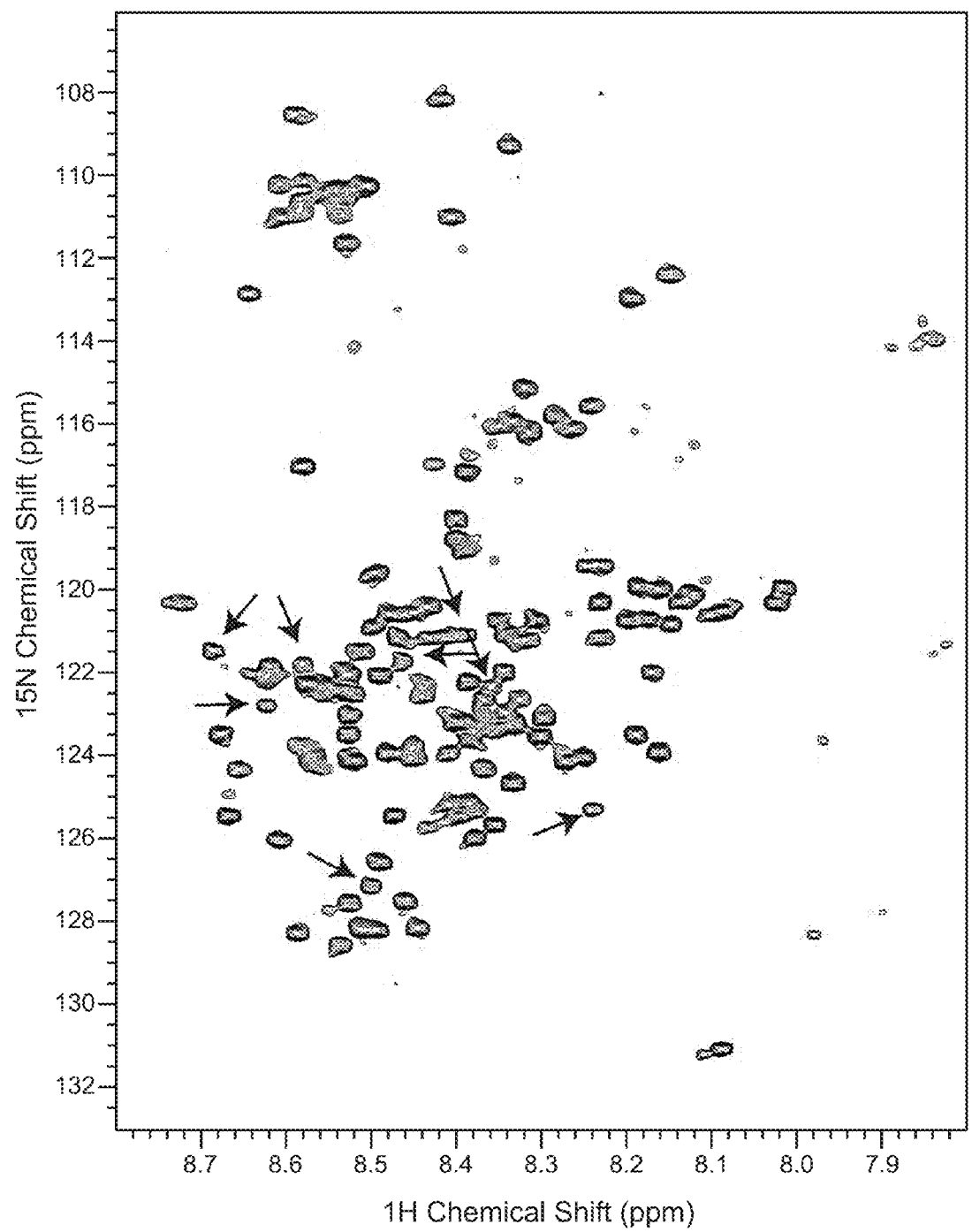

The binding epitope of anti-α-synuclein monoclonal antibody 13F3 Fab described above was further confirmed by addition of a synthetic peptide having the amino acid sequence EGAPQEGILEDMPVDPDNE (SEQ ID NO:22) corresponding to amino acid residues 105-123 in human α-synuclein. Addition of this (unlabeled) peptide to the Fab-α-synuclein complex sample in NMR experiments (as described above) resulted in reappearance of the epitope signals. (Compare FIGS. 10A and 10B.)

Figure 11A:
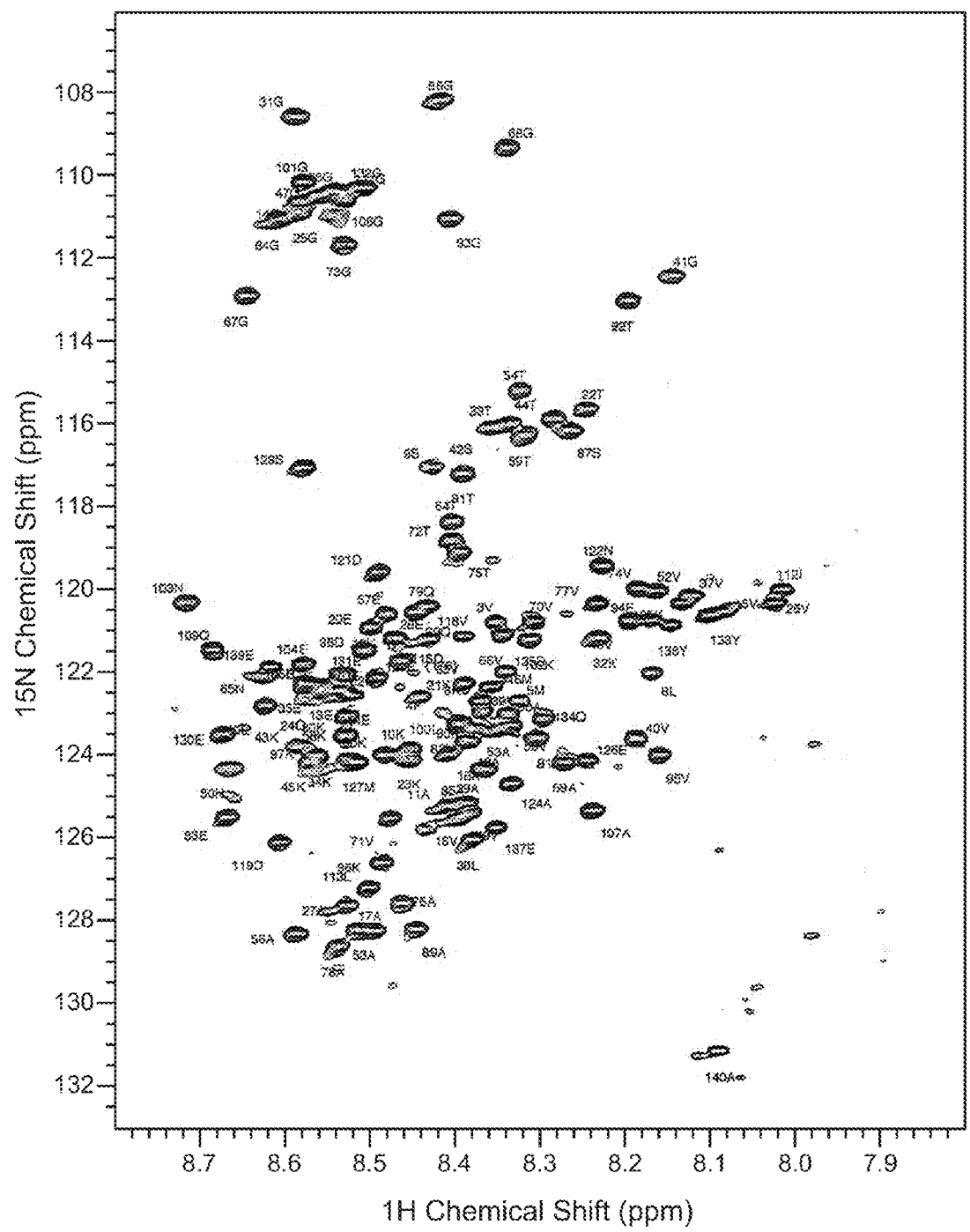
FIGS. 11A and 11B set forth data showing NMR spectra of anti-α-synuclein monoclonal antibody 1F7 Fab binding to recombinant human α-synuclein alone and with a molar ration of 1:0.5, respectively.
Figure 11B:
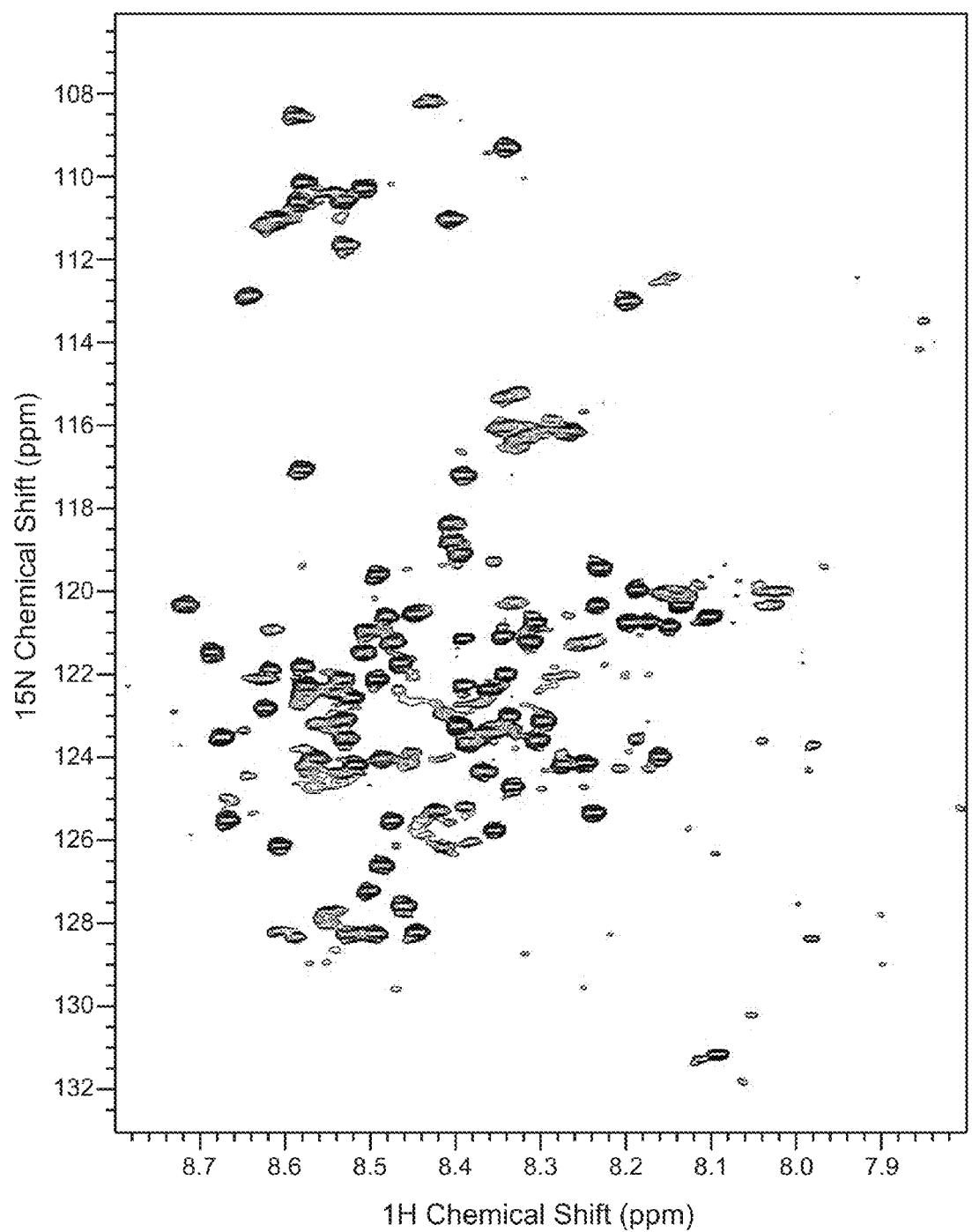

NMR results for the binding of anti-α-synuclein monoclonal antibody 1F7 Fab were as follows Preparation of this antibody bound form of α-synuclein was achieved analogous to that described above for anti-α-synuclein antibody 13F3 by addition of the Fab 1F7 to the NMR sample. 2D HSQC-TROSY spectra were recorded at increasing concentration of Fab and the proton-amide cross peak intensity monitored. Spectra of α-synuclein alone and with a molar ration of 1:0.5 are shown in FIGS. 11A and 11B, respectively. The amino acid residues showing signal decay (amino acid residues 5, 8-9, 15-22, 28, 39-43, and 78 of human α-synuclein) were classified as binding epitope of monoclonal antibody 1F7. (See Table 3 below.)

TABLE 3

| Fab | Epitope (human α-synuclein amino acid residue number) | Amino Acid Residue (human α-synuclein amino acid residue number) |
|---|---|---|
| 13F3 | 104-118 | 104-105, 107, 109-111, 113-116, 118 |
| 1F7 | 5-43 (5-78) | 5, 8-9, 15-22, 28, 39-43, 78 |

Figure 12A:
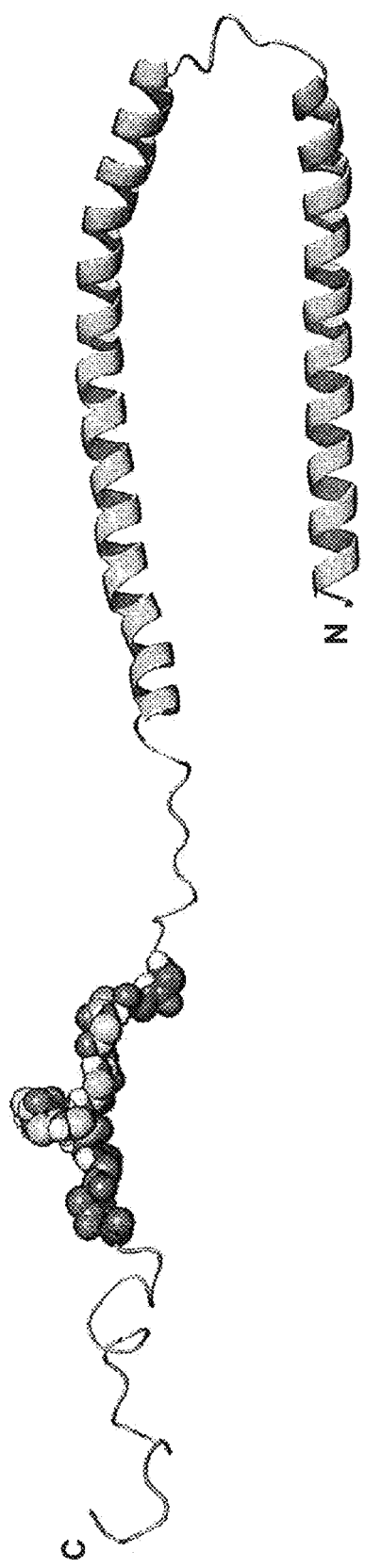
FIGS. 12A and 12B show binding epitopes of anti-α-synuclein monoclonal antibody 13F3 and anti-α-synuclein monoclonal antibody 1F7, respectively, within a schematic representation of human α-synuclein protein.
Figure 12B:
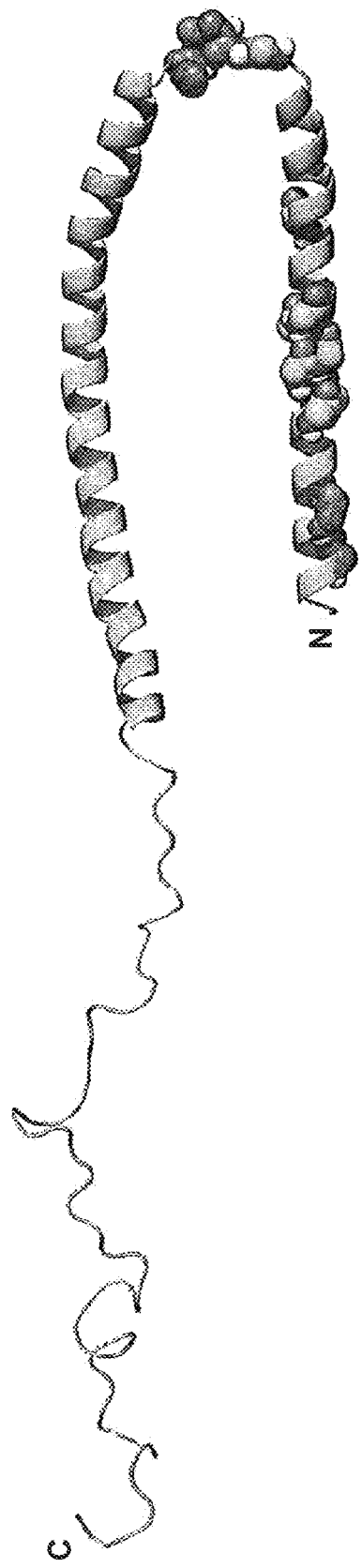

These amino acid residues were mapped to the solution structure of α-synuclein reported by Ulmer et al. and submitted to the Protein Data Bank under the submission number 1XQ8. (See Bernstein et al (1977) J Mol Biol 112:535.) The mapped epitope for anti-α-synuclein monoclonal antibody 13F3 Fab to the solution structure of α-synuclein is shown in FIG. 12A. The mapped epitope for anti-α-synuclein monoclonal antibody 1F7 Fab to the solution structure of α-synuclein is shown in FIG. 12B.

EXAMPLE 6

Identification of a Binding Epitope of Anti-α-Synuclein Monoclonal Antibody 1F7 by Peptide Mapping Using a series of 15-mer peptides spanning the length of human α-synuclein, anti-α-synuclein antibody 1F7 was found to bind to a peptide corresponding to amino acid residues 37-51 of human α-synuclein. (VLYVGSKTKEG-VVHG; SEQ ID NO:20)

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated anti-α-synuclein antibody comprising three heavy chain hypervariable regions (HVR-H1, HVR-H2, and HVR-H3) and three light chain hypervariable regions (HVR-L1, HVR-L2, and HVR-L3), wherein:
   (a) HVR-H1 comprises the amino acid sequence of SEQ ID NO:9;
   (b) HVR-H2 comprises the amino acid sequence of SEQ ID NO:10;
   (c) HVR-H3 comprises the amino acid sequence of SEQ ID NO:11;
   (d) HVR-L1 comprises the amino acid sequence of SEQ ID NO:6;
   (e) HVR-L2 comprises the amino acid sequence of SEQ ID NO:7; and
   (f) HVR-L3 comprises the amino acid sequence of SEQ ID NO:8.

2. The isolated anti-α-synuclein antibody of claim 1, comprising a heavy chain variable region and a light chain variable region, wherein the heavy chain variable region comprises the amino acid sequence of SEQ ID NO:3, and the light chain variable region comprises the amino acid sequence of SEQ ID NO:2.

3. The isolated anti-α-synuclein antibody of claim 1, comprising a light chain variable region comprising the amino acid sequence of SEQ ID NO:2.

4. The isolated anti-α-synuclein antibody of claim 1, comprising a heavy chain variable region comprises the amino acid sequence of SEQ ID NO:3.

5. An isolated anti-α-synuclein antibody comprising three heavy chain hypervariable regions (HVR-H1, HVR-H2, and HVR-H3) and three light chain hypervariable regions (HVR-L1, HVR-L2, and HVR-L3), wherein:
   (a) HVR-H1 comprises the amino acid sequence of SEQ ID NO:15;
   (b) HVR-H2 comprises the amino acid sequence of SEQ ID NO:16;
   (c) HVR-H3 comprises the amino acid sequence of SEQ ID NO:17;
   (d) HVR-L1 comprises the amino acid sequence of SEQ ID NO:12;
   (e) HVR-L2 comprises the amino acid sequence of SEQ ID NO:13; and
   (f) HVR-L3 comprises the amino acid sequence of SEQ ID NO:14.

6. The isolated anti-α-synuclein antibody of claim 5, comprising a heavy chain variable region and a light chain variable region, wherein the heavy chain variable region comprises the amino acid sequence of SEQ ID NO:5, and the light chain variable region comprises the amino acid sequence of SEQ ID NO:4.

7. The isolated anti-α-synuclein antibody of claim 5, comprising a light chain variable region comprising the amino acid sequence of SEQ ID NO:4.

8. The isolated anti-α-synuclein antibody of claim 5, comprising a heavy chain variable region comprises the amino acid sequence of SEQ ID NO:5.

9. The antibody of claim 1 or claim 5, wherein the antibody is a monoclonal antibody.

10. The antibody of claim 1 or claim 5, wherein the antibody is a human, humanized, or chimeric antibody.

11. The antibody of claim 1 or claim 5, wherein the antibody binds an α-synuclein selected from the group consisting of monomeric α-synuclein and oligomeric α-synuclein.

12. The antibody of claim 1 or claim 5 for use in reducing aggregation or oligomerization of α-synuclein.

13. The antibody of claim 2 or claim 6 for use in reducing aggregation or oligomerization of α-synuclein.

14. A pharmaceutical formulation comprising the antibody of claim 1 or claim 2 and a pharmaceutically acceptable carrier.

15. A pharmaceutical formulation comprising the antibody of claim 5 or claim 6 and a pharmaceutically acceptable carrier.

16. The antibody of claim 1 or claim 5 for use in treating or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1.

17. The antibody of claim 2 or claim 6 for use in treating or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1.

18. The antibody of claim 1 or claim 5 for use as a medicament.

19. The antibody of claim 2 or claim 6 for use as a medicament.

20. An isolated nucleic acid encoding the antibody of claim 1 or claim 5.

21. An isolated nucleic acid encoding the antibody of claim 2 or claim 6.

22. A host cell comprising the nucleic acid of claim 20.

23. A method of producing an antibody comprising culturing the host cell of claim 22 so that the antibody is produced.

24. A method for treating an individual having a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1, the method comprising administering to the individual an effective amount of the antibody of claim 1 or claim 5.

25. A method for treating an individual having a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1, the method comprising administering to the individual an effective amount of the antibody of claim 2 or claim 6.

26. A method for treating or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1, the method comprising administering to an individual in need thereof an effective amount of the antibody of claim 1 or claim 5.

27. A method for treating or delaying the onset of a disorder selected from the group consisting of a synucleinopathy, Parkinson's disease, Parkinson's disease dementia, dementia with Lewy bodies, Lewy body disease, juvenile-onset generalized neuroaxonal dystrophy (Hallervorden-Spatz disease), multiple system atrophy, pure autonomic failure, and neurodegeneration with brain iron accumulation type-1, the method comprising administering to an individual in need thereof an effective amount of the antibody of claim 2 or claim 6.

* * * * *

```
SEQUENCE LISTING

<160> NUMBER OF SEQ ID NOS: 22

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45
```

```
Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Val
                 85                  90                  95

Thr His Phe Pro His Thr Phe Gly Gly Gly Thr Lys Leu Glu Ile Lys
                100                 105                 110

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Tyr
                20                  25                  30

Tyr Met Asp Trp Val Lys Gln Arg Thr Glu Gln Gly Leu Glu Trp Ile
                35                  40                  45

Ala Arg Ile Asp Pro Glu Asp Gly Glu Thr Lys Tyr Ala Pro Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Arg Val Phe Asp Tyr Trp Gly Gln Gly Thr Thr Leu Thr Val Ser Ser
                100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Gly Gly Thr Arg Leu Glu Ile Lys
                100                 105                 110

<210> SEQ ID NO 5
```

<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Lys Arg Pro Gly Gln Gly Leu Glu Trp Ile
        35                  40                  45

Gly Asp Ile Ser Pro Gly Ser Gly Ser Thr His Tyr Asn Glu Lys Phe
    50                  55                  60

Lys Ser Lys Ala Thr Leu Thr Val Asp Thr Ser Ser Ser Thr Ala Tyr
65                  70                  75                  80

Ile Gln Leu Phe Ser Leu Thr Ser Glu Asp Ser Ala Val Tyr Tyr Cys
                85                  90                  95

Ala Ile Ala Gln Thr Thr Phe Ala Tyr Trp Gly Gln Gly Thr Leu Val
            100                 105                 110

Thr Val Ser Ala
        115

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ser Ser Gln Ser Leu Leu Asp Ser Asp Gly Lys Thr Tyr Leu Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Val Ser Lys Leu Asp Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Gln Val Thr His Phe Pro His Thr
1               5

<210> SEQ ID NO 9
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 9

Asp Tyr Tyr Met Asp
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ile Asp Pro Glu Asp Gly Glu Thr Lys Tyr Ala Pro Lys Phe Gln
1               5                   10                  15
Gly

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Asp Tyr
1

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Ser Gln Ser Ile Val His Ser Asn Gly Asn Thr Tyr Leu Glu
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Val Ser Asn Arg Phe Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Phe Gln Gly Ser His Val Pro Pro Thr
1               5
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Ser Tyr Trp Ile Thr
1               5
```

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Asp Ile Ser Pro Gly Ser Gly Ser Thr His Tyr Asn Glu Lys Phe Lys
1               5                   10                  15

Ser
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ala Gln Thr Thr Phe Ala Tyr
1               5
```

<210> SEQ ID NO 18
<211> LENGTH: 78
<212> TYPE: PRT
<213> ORGANISM: Homo sapiens

<400> SEQUENCE: 18

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala
65                  70                  75
```

<210> SEQ ID NO 19
<211> LENGTH: 43
<212> TYPE: PRT
<213> ORGANISM: Homo sapiens

<400> SEQUENCE: 19

```
Met Asp Val Phe Met Lys Gly Leu Ser Lys Ala Lys Glu Gly Val Val
```

```
                1               5                  10                 15
Ala Ala Ala Glu Lys Thr Lys Gln Gly Val Ala Glu Ala Ala Gly Lys
                    20                  25                 30

Thr Lys Glu Gly Val Leu Tyr Val Gly Ser Lys
        35                  40

<210> SEQ ID NO 20
<211> LENGTH: 15
<212> TYPE: PRT
<213> ORGANISM: Homo sapiens

<400> SEQUENCE: 20

Val Leu Tyr Val Gly Ser Lys Thr Lys Glu Gly Val Val His Gly
1               5                  10                  15

<210> SEQ ID NO 21
<211> LENGTH: 18
<212> TYPE: PRT
<213> ORGANISM: Homo sapiens

<400> SEQUENCE: 21

Gly Lys Asn Glu Glu Gly Ala Pro Gln Glu Gly Ile Leu Glu Asp Met
1               5                  10                  15

Pro Val

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Gly Ala Pro Gln Glu Gly Ile Leu Glu Asp Met Pro Val Asp Pro
1               5                  10                  15

Asp Asn Glu
```